(12) United States Patent
Avrahami et al.

(10) Patent No.: US 6,611,706 B2
(45) Date of Patent: Aug. 26, 2003

(54) MONOPOLAR AND BIPOLAR CURRENT APPLICATION FOR TRANSDERMAL DRUG DELIVERY AND ANALYTE EXTRACTION

(75) Inventors: Zohar Avrahami, Rehovot (IL); Ze'ev Sohn, Ginot Shomron (IL)

(73) Assignee: Transpharma Ltd., Yehud (IL)

( * ) Notice: Subject to any disclaimer, the term of this patent is extended or adjusted under 35 U.S.C. 154(b) by 0 days.

(21) Appl. No.: 09/859,645

(22) Filed: May 17, 2001

(65) Prior Publication Data

US 2002/0058936 A1 May 16, 2002

Related U.S. Application Data

(60) Continuation-in-part of application No. 09/635,892, filed on Aug. 10, 2000, which is a division of application No. 09/189,170, filed on Nov. 9, 1998, now Pat. No. 6,148,232.

(51) Int. Cl.[7] ............................... A61N 1/30; A61B 5/04
(52) U.S. Cl. ........................................ 604/20; 600/372
(58) Field of Search .................... 604/19–21; 607/2, 607/3, 152; 600/391, 372

(56) References Cited

U.S. PATENT DOCUMENTS

| | | |
|---|---|---|
| 3,964,482 A | 6/1976 | Grestel |
| 4,775,361 A | 10/1988 | Jacques et al. |
| 4,943,290 A | 7/1990 | Rexroth et al. |
| 5,019,034 A | 5/1991 | Weaver et al. |
| 5,135,478 A | 8/1992 | Sibalis |
| 5,165,418 A | 11/1992 | Tankovich |
| 5,196,709 A | 3/1993 | Berndt et al. |
| 5,232,441 A | 8/1993 | Stephen et al. |
| 5,246,867 A | 9/1993 | Lakowicz et al. |
| 5,281,825 A | 1/1994 | Berndt et al. |

(List continued on next page.)

FOREIGN PATENT DOCUMENTS

| | | | |
|---|---|---|---|
| EP | 0547 482 | 6/1993 | ............ A61N/1/30 |
| WO | WO 93/10854 | 6/1993 | ............ A61N/1/30 |
| WO | WO 94/16765 | 8/1994 | ............ A61N/1/30 |
| WO | WO 94/27671 | 12/1994 | ............ A61N/1/30 |
| WO | WO 97/07734 | 3/1997 | ............ A61B/5/00 |
| WO | WO00/69515 | 11/2000 | |
| WO | WO00/74767 | 12/2000 | |

OTHER PUBLICATIONS

Henry et al., "Micromachined needles for the transdermal delivery of drug", IEEE 11th Annual International Workshop on Micro–Electro–Mechanical Systems, 1998, pp. 494–498.
Chizmadzhev, et al., "Electrical properties of skin at moderate voltages", Biophysics Journal, Feb. 1998, 74(2), pp. 843–856.

(List continued on next page.)

*Primary Examiner*—Sharon Kennedy
(74) *Attorney, Agent, or Firm*—Abelman, Frayne & Schwab

(57) ABSTRACT

A device for facilitating transdermal passage of a substance through skin on the body of a subject is provided. The device preferably includes afcn electrode and a control unit. In a preferred embodiment, the control unit is adapted to drive the electrode to apply to the skin a current capable of ablating stratum corneum epidermidis of the skin, so as to facilitate transdermal passage of the substance. The control unit detects generation of at least one spark responsive to application of the current, and modifies a parameter of the current responsive to detecting the generation of the at least one spark.

15 Claims, 12 Drawing Sheets

U.S. PATENT DOCUMENTS

| | | | | |
|---|---|---|---|---|
| 5,328,452 | A | 7/1994 | Sibalis | |
| 5,380,272 | A | 1/1995 | Gross | |
| 5,409,835 | A | 4/1995 | Lakowicz et al. | |
| 5,421,817 | A | 6/1995 | Liss et al. | |
| 5,423,803 | A | 6/1995 | Tankovich et al. | |
| 5,439,440 | A | 8/1995 | Hofmann | |
| 5,458,140 | A | 10/1995 | Eppstein et al. | |
| 5,462,520 | A | 10/1995 | Hofmann | 604/20 |
| 5,464,386 | A | 11/1995 | Hofmann | 604/20 |
| 5,485,530 | A | 1/1996 | Lakowicz et al. | |
| 5,500,437 | A | 3/1996 | Saitoh et al. | |
| 5,571,149 | A | 11/1996 | Liss et al. | |
| 5,582,168 | A | 12/1996 | Samuels et al. | |
| 5,624,847 | A | 4/1997 | Lakowicz et al. | |
| 5,628,310 | A | 5/1997 | Rao et al. | |
| 5,631,169 | A | 5/1997 | Lakowicz et al. | |
| 5,648,269 | A | 7/1997 | Lakowicz et al. | |
| 5,660,991 | A | 8/1997 | Lakowicz et al. | |
| 5,674,267 | A | 10/1997 | Mir et al. | |
| 5,688,232 | A | 11/1997 | Flower | |
| 5,688,233 | A | 11/1997 | Hofmann | 604/20 |
| 5,697,896 | A | 12/1997 | McNichols et al. | |
| 5,720,772 | A | 2/1998 | Eckhouse | |
| 5,722,397 | A | 3/1998 | Eppstein | |
| 5,759,767 | A | 6/1998 | Lakowicz et al. | |
| 5,792,049 | A | 8/1998 | Eppstein et al. | |
| 5,860,421 | A | 1/1999 | Epstein et al. | |
| 5,871,469 | A | 2/1999 | Eggers et al. | |
| 5,885,211 | A | 3/1999 | Eppstein et al. | |
| 5,902,272 | A | 5/1999 | Eggers et al. | |
| 5,911,223 | A | 6/1999 | Weaver et al. | |
| 5,924,981 | A | 7/1999 | Rothfritz et al. | |
| 5,938,657 | A | 8/1999 | Assa et al. | |
| 5,964,726 | A | 10/1999 | Korenstein et al. | |
| 5,983,130 | A | 11/1999 | Phipps et al. | |
| 5,983,131 | A | 11/1999 | Weaver et al. | |
| 6,002,482 | A | 12/1999 | Rothfritz et al. | |
| 6,009,344 | A | 12/1999 | Flower et al. | |
| 6,022,316 | A | 2/2000 | Eppstein et al. | |
| 6,024,733 | A | 2/2000 | Eggers et al. | |
| 6,030,399 | A | 2/2000 | Ignotz et al. | |
| 6,041,253 | A | 3/2000 | Kost et al. | |
| 6,045,502 | A | 4/2000 | Epstein et al. | |
| 6,050,988 | A | 4/2000 | Zuch | |
| 6,055,451 | A | 4/2000 | Bambot et al. | |
| 6,066,134 | A | 5/2000 | Eggers et al. | |
| 6,076,012 | A | 6/2000 | Swanson et al. | |
| 6,083,196 | A | 7/2000 | Trautman et al. | |
| 6,088,606 | A | 7/2000 | Ignotz et al. | |
| 6,090,106 | A | 7/2000 | Goble et al. | |
| 6,104,952 | A | 8/2000 | Tu et al. | |
| 6,117,109 | A | 9/2000 | Eggers et al. | |
| 6,142,939 | A | 11/2000 | Eppstein et al. | |
| 6,142,992 | A | 11/2000 | Cheng et al. | |
| 6,148,232 | A | 11/2000 | Avrahami | |
| 6,159,194 | A | 12/2000 | Eggers et al. | |
| 6,173,202 | B1 | 1/2001 | Eppstein et al. | |
| 6,183,434 | B1 | 2/2001 | Eppstein | |
| 6,192,734 | B1 | 2/2001 | Rothfritz et al. | |
| 6,210,402 | B1 | 4/2001 | Olsen et al. | |
| 6,228,078 | B1 | 5/2001 | Eggers et al. | |
| 6,235,020 | B1 | 5/2001 | Cheng et al. | |
| 6,238,391 | B1 | 5/2001 | Olsen et al. | |

OTHER PUBLICATIONS

"Instructions Manual for the Force 2 Electrosurgical Generator", Valleylab/TycoHealthcare Group LP, Boulder, Colorado, 1999.

U.S. patent application Ser. No.: 09/840,522, entitled: "Handheld apparatus and method for transdermal drug delivery and analyte extraction", filed Apr. 23, 2001.

U.S. patent application Ser. No.: 09/859,646, entitled: "Electronic card for transdermal drug delivery and analyte extraction", filed May 17, 2001.

U.S. patent application Ser. No. 10/021,586.

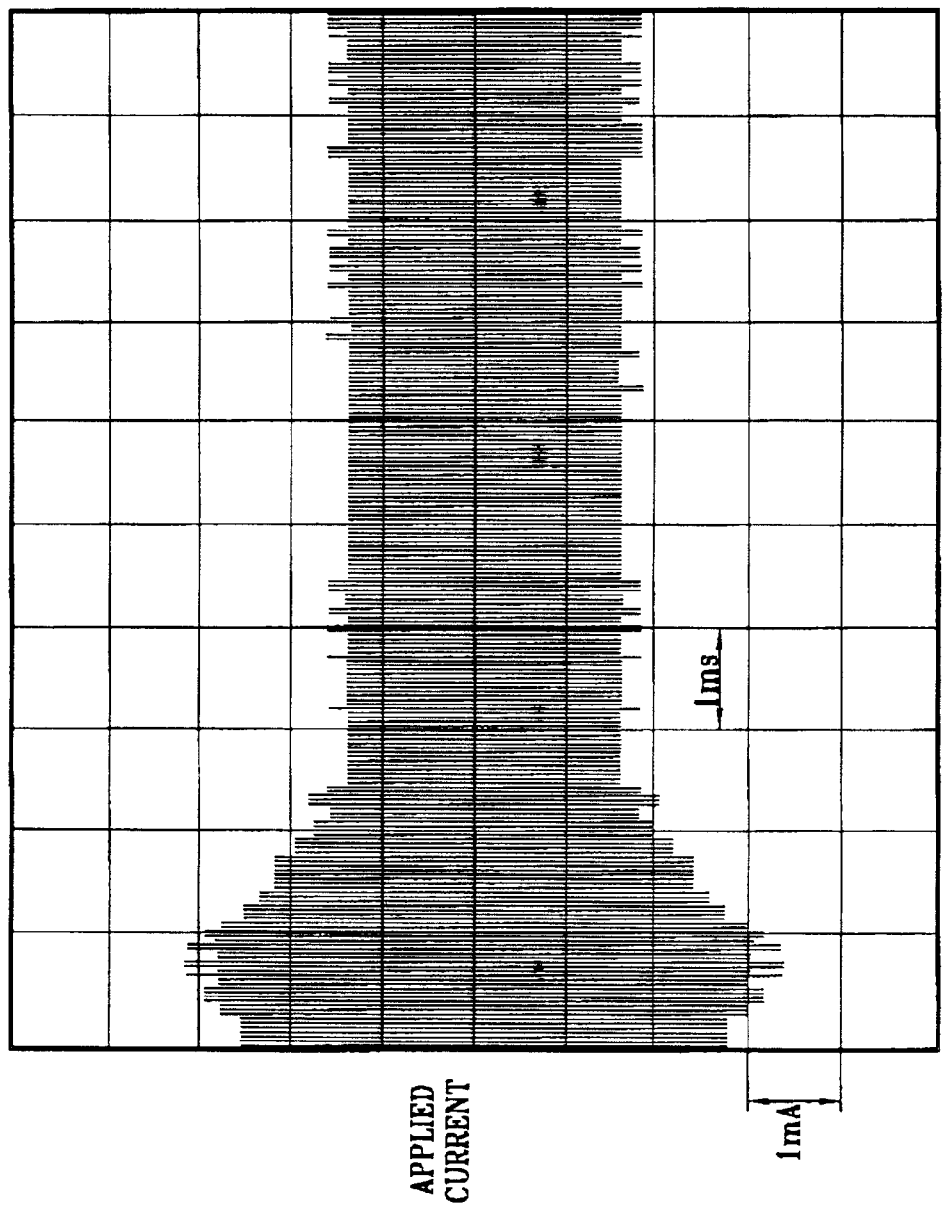

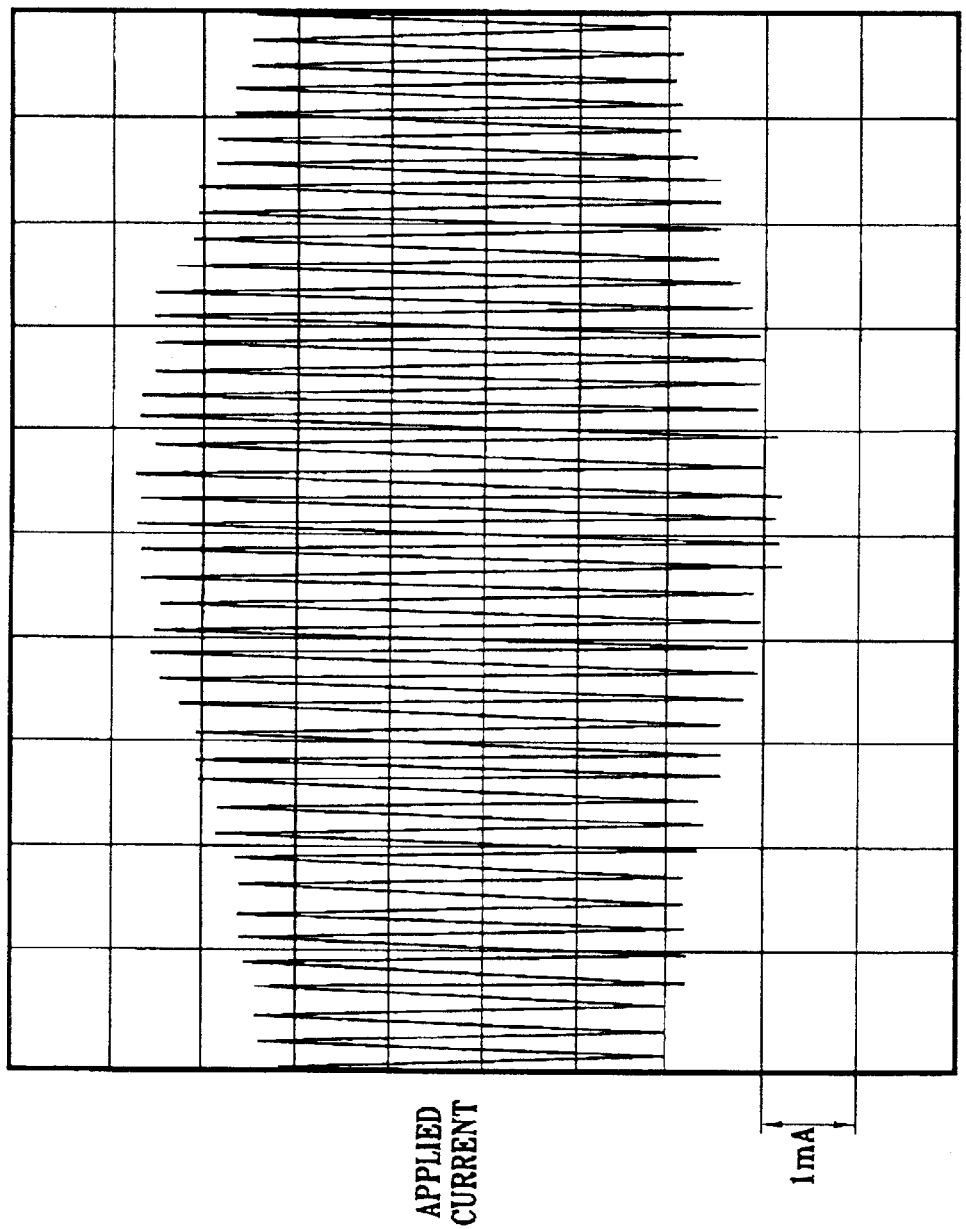

MONOPOLAR AND BIPOLAR CURRENT APPLICATION FOR TRANSDERMAL DRUG DELIVERY AND ANALYTE EXTRACTION

CROSS-REFERENCE TO RELATED APPLICATIONS

This application is a continuation-in-part of U.S. patent application Ser. No. 09/635,892, entitled, "Transdermal drug delivery and analyte extraction," filed Aug. 10, 2000, which is a divisional based on U.S. patent application Ser. No, 09/189,170 (now U.S. Pat. No. 6,148,232), filed Nov. 9, 1998, entitled, "Transdermal drug delivery and analyte extraction." Both of these applications share common inventorship with the inventorship of the present patent application and are incorporated herein by reference.

FIELD OF THE INVENTION

The present invention relates generally to methods and devices for drug delivery and analyte extraction, and specifically to methods and devices for puncturing the outer layer of living skin and to methods and devices for transdermal drug delivery and analyte extraction.

BACKGROUND OF THE INVENTION

A number of different methods have been developed to perform transdermal drug delivery and/or analyte extraction, including passive diffusion of a drug or analyte between a skin patch and skin, as well as active processes such as iontophoresis, sonophoresis, electroporation, and chemically enhanced diffusion. These methods are primarily used for generating transdermal movement of small molecules, but generally do not enhance the motion of large molecules through the 10–50 micron thick outermost layer of the skin, the stratum corneum epidermidis.

In an article, "Micromachined needles for the transdermal delivery of drugs," IEEE 11th Annual International Workshop on Micro-Electro-Mechanical Systems (1998), pp. 494–498, which is incorporated herein by reference, Henry et al. discuss a method of mechanically puncturing the skin with microneedles in order to increase the permeability of skin to a test drug. In the article, microfabrication techniques are described to etch an array of needles in silicon, and experiments performed on cadaver skin with the needle array demonstrated an increase in permeability subsequent to puncture of the skin. The needles are created with a predetermined length, and penetrate to the same depth from the skin surface, regardless of the local thickness of the stratum corneum. It is known that if the needles are longer than the local thickness, then the underlying epidermal tissue may be injured, while if the needles are too short, channel formation through the stratum corneum may be incomplete.

U.S. Pat. No. 4,775,361 to Jacques et al., U.S. Pat. No. 5,165,418 to Tankovich, and U.S. Pat. No. 5,423,803 to Tankovich et al., and PCT Publication WO 97/07734 to Eppstein et al., which are incorporated herein by reference, describe methods of using laser pulses to locally heat the stratum corneum to about 120° C., thereby causing local ablation, in order to cause a single hole to develop in the stratum corneum through which large molecules may pass. Whereas some selectivity of ablation depth can be attained by varying the wavelength of the laser pulse, no feedback mechanism is disclosed whereby the laser pulses are terminated upon generation of the necessary damage to the stratum corneum.

PCT Publication WO 97/07734 also discloses thermal ablation of the stratum corneum using an electrically resistive element in contact with the stratum corneum, such that a high current through the element causes a general heating of tissue in its vicinity, most particularly the stratum corneum. As above, no means are disclosed to terminate current flow upon sufficient disruption of the stratum corneum. Additionally, thermal characteristics of skin vary highly across different areas of an individual's skin, as well as among a group of subjects, making optimal thermal dosages, which produce the desired ablation without causing pain, very difficult to determine.

Electroporation is also well known in the art as a method to increase pore size by application of an electric field. This process is described in an article by Chizmadzhev et al., entitled "Electrical properties of skin at moderate voltages," *Biophysics Journal*, February, 1998, 74(2), pp. 843–856, which is incorporated herein by reference. Electroporation is disclosed as a means for transiently decreasing the electrical resistance of the stratum corneum and increasing the transdermal flux of small molecules by applying an electric field to increase the size of existing pores. Electroporation generally does not produce pores of sufficient diameter to pass large molecules therethrough. Additionally, optimal voltage profiles are difficult to determine because of naturally occurring variations as described hereinabove, as well as the lack of an accurate feedback mechanism to indicate achievement of the desired pore enlargement. If excessive voltage is applied, an irreversible breakdown occurs, resulting in damage to the skin and possible sensations of pain.

U.S. Pat. No. 5,019,034 to Weaver et al., which is incorporated herein by reference, describes apparatus for applying high voltage, short duration electrical pulses on the skin to produce electroporation, and states that " . . . reversible electrical breakdown . . . along with an enhanced tissue permeability, is the characteristic effect of electroporation."

U.S. Pat. Nos. 5,885,211, 6,022,316, 6,142,939 and 6,173,202 to Eppstein et al., which are incorporated herein by reference, describe methods for forming micropores in the stratum corneum by heating tissue-bound water above the vapor point with a heat conducting element, so as to enhance transdermal transport of an analyte or active substance. Further enhancement techniques include the use of sonic energy, pressure, and chemical enhancers.

U.S. Pat. No. 3,964,482 to Gerstel, U.S. Pat. No. 6,050,988 to Zuck, and U.S. Pat. No. 6,083,196 to Trautman et al., which are incorporated herein by reference, describe other apparatus and methods for facilitating transdermal movement of a substance.

U.S. Pat. No. 6,148,232 to Avrahami, which is incorporated herein by reference, describes apparatus for applying electrodes at respective points on skin of a subject and applying electrical energy between two or more of the electrodes to cause resistive heating and subsequent ablation of the stratum corneum primarily in an area intermediate the respective points. Various techniques for limiting ablation to the stratum corneum are described, including spacing of the electrodes and monitoring the electrical resistance of skin between adjacent electrodes.

Electrosurgery is commonly used during surgical procedures today, particularly in endoscopic and laparoscopic surgery where direct access to the tissue being dissected is limited. Electrosurgery involves applying radio frequency electric current to electrodes which are used to sever tissue or achieve homeostasis. A publication entitled "Instruction Manual for the Force 2 Electrosurgical Generator" (Valleylab/Tyco Healthcare Group LP, Boulder, Colo.), which is incorporated herein by reference, describes the modes of operation of electrosurgical devices.

Three surgical effects can be achieved with electrosurgery. At relatively low power settings, current passing through tissue causes heating of the tissue due to the high frequency and the electrical resistance thereof. As the tissue is heated, water within the tissue is driven out, leading to desiccation of the tissue. At higher power levels, the water in the tissue may vaporize before it leaves the cells, causing the cells to explode. Moving the electrode into contact with new tissue causes new cells to explode, and results in electrosurgical cutting. Alternatively, small sparks may jump across gaps, causing cells to explode or ablate. Due to the extreme concentration of current, the cutting is particularly efficient with short sparks.

Applying electrical power intermittently, having higher peak voltages but the same average power as is used in electrosurgical cutting, allows for desiccation of the tissue near the electrode without bursting the cells. As water leaves the cells, the resistance of the cells increases until the resistance of the tissue is greater than that of the medium surrounding the tissue and electrode. If the peak voltage is high enough, a long spark may occur between the electrode and surrounding tissue (where minimal desiccation has occurred). The spark causes charring and cauterization of the tissue, the degree of which is determined by the length of time sparks have impinged the tissue.

U.S. Pat. No. 6,159,194 to Eggers et al., which is incorporated herein by reference, describes electrosurgical apparatus and methods for inducing tissue contraction, without ablation or dissociation of surrounding tissue, in order to reduce wrinkles in skin.

U.S. Pat. No. 6,090,106 to Goble et al., which is incorporated herein by reference, describes monopolar and bipolar electrosurgical instruments for ablating gross tissue, such as the prostate or endometrial tissue.

U.S. Pat. Nos. 6,066,134 and 6,024,733 to Eggers et al., which are incorporated herein by reference, describe electrosurgical apparatus and methods for ablating outer layers of skin for the treatment of unwanted tissue pigmentations, melanomas, and other skin disorders.

U.S. Pat. No. 4,943,290 to Rexroth et al., which is incorporated herein by reference, describes electrosurgical apparatus in which a nonconductive fluid is transported to the region of the electrode to isolate the electrode and prevent undesirable damage of surrounding tissue.

SUMMARY OF THE INVENTION

It is an object of some aspects of the present invention to provide improved apparatus and methods for transdermal delivery of an active substance.

It is a further object of some aspects of the present invention to provide improved apparatus and methods for transdermal analyte extraction.

It is yet a further object of some aspects of the present invention to provide improved apparatus and methods for creating narrow channels through the stratum corneum of living skin by puncturing.

It is still a further object of some aspects of the present invention to provide improved apparatus and methods for reducing sensation and minimizing damage to skin underlying the stratum corneum during channel creation.

It is an additional object of some aspects of the present invention to provide improved apparatus and methods for controlling the timing of channel creation.

It is another object of some aspects of the present invention to provide improved apparatus and methods for puncturing the skin and/or transdermally delivering an active substance and/or transdermally extracting an analyte, using a miniature, self-contained device.

It is yet another object of some aspects of the present invention to provide improved apparatus and methods for transdermally delivering an active substance using a standard medical skin patch.

In preferred embodiments of the present invention, a device for enhancing transdermal movement of a substance comprises: (a) a housing, for supporting at least one spark-generating electrode in a vicinity of the skin of a subject; and (b) a control unit, coupled to the housing, which causes electrical current to pass through the electrode and generate one or more sparks between the electrode and the stratum corneum epidermidis, in order to create at least one micro-channel in the stratum corneum to enable or augment transdermal movement of the substance. Preferably, the control unit comprises circuitry to control the magnitude, frequency, and/or duration of the electrical energy delivered to the electrode, so as to control spark generation, and thus micro-channel formation.

Alternatively or additionally, current may be applied to the skin in order to ablate the stratum corneum, substantially without causing sparks until the ablation has reached a certain depth. In this case, spark generation may be used as a form of feedback, which indicates that the desired depth has been reached and current application should be terminated. For these applications, the electrodes are preferably shaped and/or supported in a housing which is conducive to facilitating ablation of the stratum corneum to the desired depth, but not beyond that depth. If appropriate, the control unit may determine whether a number of sparks or a rate of spark generation exceeds a threshold number or rate, and terminate or reduce current application responsive thereto.

The term "micro-channel" as used in the context of the present patent application refers to a pathway generally extending from the surface of the skin through all or a significant part of the stratum corneum, through which pathway molecules can diffuse. Preferably, micro channels allow the diffusion therethrough of large molecules at a greater rate than the same molecules would diffuse through pores generated by electroporation.

It is believed that such micro-channels are formed, in accordance with a preferred embodiment of the present invention, due to spark generation between the electrode and the skin as a result of sufficiently large applied voltages. Unlike many methods of electrically-promoted drug delivery known in the art, such as iontophoresis and electroporation, this embodiment of the present invention enables relatively large channels to be formed, through which even large molecules of the active substance can pass rapidly, without the necessity of ionizing or polarizing the molecules. Moreover, unlike the device described in the above-cited U.S. Pat. No. 6,148,232 to Avrahami, which does describe the creation of micro-channels in the stratum corneum, this particular embodiment preferably creates the channels in the stratum corneum by generating sparks which generally explosively remove the stratum corneum in a very localized area, in a manner analogous to that used in electrosurgery. Nevertheless, it is to be understood that, for certain applications, some of the apparatus and techniques described in the Avrahami patent may be adapted for use with preferred embodiments of the present invention, mutatis mutandis. In particular, as described herein, electric current may be applied to the skin in order to ablate the stratum corneum, without necessarily generating sparks, using some of the same parameters (e.g., frequency or amplitude) as those described in the Avrahami patent.

In general, the stratum corneum epidermidis (the superficial layer of the epidermis) demonstrates a significantly higher resistance to the passage of molecules therethrough than does the underlying epidermal tissue. It is therefore an object of these preferred embodiments of the present invention to form micro-channels in the stratum corneum by ablating the stratum corneum, in order to increase conductance of the substance therethrough, and to generally not directly affect or damage epidermal tissue underlying the stratum corneum or in the innervated dermis. Limiting ablation substantially to the non-innervated stratum corneum is expected to decrease or eliminate the subject's sensations, discomfort, or pain responsive to use of these embodiments of the present invention, particularly as compared with other procedures known in the art. It is noted, however, that for some applications it may be desirable to ablate tissue to a depth beyond the stratum corneum.

In some preferred embodiments of the present invention, the housing supports an array of electrodes, preferably closely-spaced electrodes, which act together to produce a high micro-channel density in an area of the skin under the housing. Preferably, the control unit and/or associated circuitry sequentially or simultaneously evaluates the current flow through each electrode, or a subset of the electrodes, in order to determine, for example: (a) when one spark or a desired number of sparks have formed responsive to the applied field, or (b) when a property (such as electrical impedance) of the skin has changed, thereby indicating successful ablation of the stratum corneum. Responsive thereto, the control unit discontinues application of the field. In a preferred embodiment, since the formation of a spark between an electrode and the skin typically leads to ablation of at least some stratum corneum, the degree of ablation is preferably controlled by allowing a predetermined number of sparks to occur. Alternatively, the total current flow to the skin is used as a control parameter. Additionally or alternatively, a strictly time-based control is used to control the degree of ablation (e.g., a predetermined voltage applied for a predetermined time).

In further preferred embodiments of the present invention, a concentric electrode pair is formed by employing the housing as a return path for the current passing from the electrode to the skin. It is to be understood that use of a conductive portion of the housing as a return path is one preferred method for achieving the goals of these embodiments of the present invention. For other applications, however electrodes coupled to the housing may be used, as well. Preferably, the housing has a relatively large contact surface area with the skin, resulting in relatively low current densities in the skin near the housing, and thus no significant heating or substantial damage to the skin at the contact surface. In proximity to the inner electrode, by contrast, the high-energy applied field typically induces very rapid heating and ablation of the stratum corneum. It will be appreciated that a plurality of inner electrodes may be provided, adjacent to or surrounded at least in part by one or more other electrodes which define the return path.

Typically, the housing is adapted to contain a pharmaceutical substance, e.g.: (a) an active substance, such as insulin or dimenhydrinate, (b) a vaccine, (c) a substance to aid in diagnosis of a condition, or (d) substantially any other pharmaceutical or other type of material suitable for transdermal administration. Following ablation at one or more sites on the skin, the substance is preferably actively or passively delivered to the ablated sites. For some applications, the active substance is in the form of a gel, which is applied to the housing near the electrodes at the time of manufacture of the device, or, as appropriate, shortly prior to the use of the device.

Alternatively, the device creates micro-channels, as described herein, and is then removed from the skin, in order to enhance the transdermal delivery of a substance into or out of a commercially-available skin patch subsequently placed on the skin.

For some applications, it is desirable to stop transdermal flow of a substance (e.g., an analyte or a drug) at a certain point after ablation of the stratum corneum. Preferably, the flow is stopped by application of a current, e.g., one having an AC and/or a DC component, which at least in part seals the pores induced in the stratum corneum. For example, the applied current may be configured so as to have a local coagulation effect, optionally using parameters known in the art of electrosurgery. Alternatively or additionally, the current may induce the coagulation of a material in the pore, such as a natural body fluid or an externally-applied material.

In some preferred embodiments of the present invention, a material is applied between the electrodes and the skin so as to aid in attaining good electrical contact between the electrodes and the skin. In particular, this embodiment is appropriate for applications in which the electrodes do not make physical contact with the skin, and instead generate sparks which ablate the stratum corneum. In a preferred application, the material comprises a liquid, gel, cream or disposable film or patch, and, if appropriate, a substance such as a drug intended for transdermal delivery.

For some applications, electrodes which substantially do not contain metal are employed to ablate the stratum corneum. Alternatively or additionally, drug films or coatings are applied to the surface of the electrodes, or are impregnated within the electrodes, and the electrodes themselves are porous or otherwise configured to allow designated materials to be delivered through the skin. Further alternatively or additionally, a charge-limiting substance for delivery into the body may be integrated into the electrode itself, so as to terminate current flow through the electrode when a sufficient quantity of the substance has been delivered.

It will be appreciated that a range of manufacturing techniques may adapted for the production of devices such as those described herein. For example, electrodes may be etched onto a printed circuit board (PCB), or they may be electroformed. If appropriate, the electrodes may be printed onto a surface, preferably incorporating a substance for transdermal delivery into the printed electrode. Alternatively or additionally, electrodes may be stamped or laser-cut out of thin sheet metal, and sandwiched between insulating spacers.

Similarly, it will be appreciated that the transdermal movement of a range of molecules may be facilitated using the techniques provided by preferred embodiments of the present invention, including both small molecules and molecules having molecular weights greater than, for example, 500 dalton. Similarly, hydrophilic molecules, which are normally rejected by the stratum corneum, are particularly well-suited for use with these embodiments. It is noted that prior art transdermal drug delivery techniques often required finding drugs that are neither hydrophilic nor hydrophobic, thus compromising to some extent the availability of many drugs for these applications.

As appropriate, methods and apparatus described in one or more of the following applications, which are assigned to the assignee of the present patent application and are incorporated herein by reference, may be adapted for use with techniques provided by some embodiments of the present invention:

A U.S. patent application entitled, "Handheld apparatus and method for transdermal drug delivery and analyte extraction," filed Apr. 23, 2001.

That application describes a device for treating skin on the body of a subject, including:
- a plurality of electrodes, which are adapted to be placed in contact with the skin and then moved across the skin while maintaining electrical contact with the skin; and
- a power source, which is adapted to apply a current between two or more of the plurality of electrodes at the same time as the electrodes are being moved across the skin.

In a preferred embodiment, the device includes a marking unit, adapted to apply a substance to the skin so as to demarcate a region of the skin to which the current is applied. Alternatively or additionally, the device includes one or more protrusive elements, adapted to press the skin so as to demarcate a region of the skin to which the current is applied.

In a preferred embodiment, the substance application unit includes:
- a spool, adapted to rotate as the device moves across the skin; and
- a substance application strip having the substance applied thereto, which strip is adapted to be disposed around the spool, so as to unwind from the spool as the device is moved across the skin, and so as to cover the site on the skin to which the current is applied.

That application also describes a device for treating skin on the body of a subject, including:
- a roller, adapted to rotate when it is moved across the skin;
- a plurality of electrodes, disposed over a surface of the roller, so as to be placed in sequence into contact with the skin as the roller is moved across the skin; and
- a power source, which is adapted to drive a current through each electrode when the electrode is in contact with the skin.

That application further describes a device for treating skin on the body of a subject, including:
- a housing;
- a plurality of electrodes, disposed on a surface of the housing, which are adapted to be placed in contact with the skin;
- a motion sensor, which is adapted to generate a sensor signal responsive to motion of the housing; and
- a control unit, which is adapted to receive the sensor signal, to determine, responsive thereto, a physical disposition of the device, and to control current flow to the plurality of electrodes responsive to determining the physical disposition.

That application still further describes a device for treating skin on the body of a subject, including:
- a plurality of receiving electrodes, which are adapted to be placed in contact with the skin so as to provide electrical contact with the skin;
- a driving electrode, which is adapted to be passed across the receiving electrodes so as to create electrical contact with a first one of the receiving electrodes prior to creating electrical contact with a second one of the receiving electrodes; and
- a power source, which is adapted to drive the driving electrode to apply a first current to the first receiving electrode when the driving electrode is in electrical contact with the first receiving electrode, and to apply a second current to the second receiving electrode when the driving electrode is in electrical contact with the second receiving electrode.

A U.S. patent application entitled, "Electronic card for transdermal drug delivery and analyte extraction," filed on even date with the present patent application.

That application describes a device for delivering a substance to skin of a subject, including:
- a substance storage unit, which is adapted to store the substance;
- an analysis unit, which is adapted to receive a portion of a body fluid of the subject, to analyze the portion, and to generate a signal responsive to the analysis of the portion;
- one or more electrodes, which are adapted to be placed at respective sites on the skin; and
- a substance delivery unit, which is adapted to receive the signal, and, responsive thereto, to drive at least some of the one or more electrodes to apply to respective ones of the sites on the skin a current capable of ablating stratum corneum epidermidis of the skin, so as to facilitate delivery of the substance from the storage to drive to apply unit through the skin at the respective ones of the sites.

In a preferred embodiment, the substance delivery unit is adapted:
- to designate at a first time a first number of the one or more electrodes to drive to apply the current, responsive to a desired rate of delivery of the substance during a first time period, and
- to designate at a second time a second number of the one or more electrodes to drive to apply the current, responsive to a desired rate of delivery of the substance during a second time period, the second number being different from the first number.

Alternatively or additionally, the device includes a sensor, adapted to measure a physiological parameter of the subject and to generate a sensor signal responsive thereto, wherein the substance delivery unit is adapted to designate the second time responsive to the sensor signal. The sensor may be adapted to measure a physiological parameter selected from the list consisting of: transepidermal water loss (TEWL), a property of the skin, temperature, blood pressure, heart rate, and respiration rate.

For some applications, at least one of the one or more electrodes is adapted to apply to the skin a substantially DC current capable of enhancing by means of iontophoresis the passage of a material through the skin.

Alternatively or additionally, the device includes a communications unit, which is adapted to receive the signal and, responsive thereto, to transmit information to a computer external to the device. Further alternatively or additionally, the device includes a communications unit, which is adapted to receive an instruction from a remote computer, and the substance delivery unit is adapted to modify, responsive to the instruction, a parameter of the current.

If appropriate, the analysis unit may be adapted to drive a subset of the one or more electrodes to apply a current to the skin, so as to facilitate extraction therefrom of an analyte in blood of the subject. Alternatively or additionally, the analysis unit may be adapted to analyze blood of the subject, urine of the subject, and/or saliva of the subject, and to generate the signal responsive thereto.

Israel Patent Application 136,008, entitled, "Electrically-mediated transdermal drug injection," filed May 7, 2000.

There is therefore provided, in accordance with a preferred embodiment of the present invention, a device for ablating stratum corneum epidermidis of skin on the body of a subject, including:
- a housing;
- a substance storage unit, adapted to store a substance;
- an electrode, coupled to the housing; and
- a control unit, which is adapted to apply electrical energy to the electrode when the electrode is in a vicinity of the skin, and to configure the energy so as to be capable of generating one or more sparks between the electrode and the skin which are capable of causing ablation of an area of the stratum corneum, so as to facilitate passage of the substance from the storage unit through the ablated area of the skin.

There is further provided, in accordance with a preferred embodiment of the present invention, a device for facilitating passage of a substance through skin on the body of a subject, including:
- an electrode;
- a housing, adapted to be placed on the skin and to support the electrode in a position not in contact with the skin; and
- a control unit, adapted to apply electrical energy to the electrode capable of ablating stratum corneum epidermidis of the skin, so as to facilitate transdermal passage of the substance.

In a preferred embodiment, the control unit is adapted to apply electrical energy capable of generating a spark between the electrode and the skin, so as to ablate the stratum corneum.

Alternatively or additionally, the device includes a conductive material, adapted for placement between the electrode and the skin so as to facilitate current flow between the electrode and the skin.

There is yet further provided, in accordance with a preferred embodiment of the present invention, a device for facilitating passage of a substance through skin on the body of a subject, including:
- an electrode;
- a housing, adapted to be placed on the skin and to support the electrode in a position in which the electrode is in contact with the skin and substantially does not extend past a plane defined by a surface of the skin; and
- a control unit, adapted to drive the electrode to apply to the skin a current capable of ablating stratum corneum epidermidis of the skin, so as to facilitate transdermal passage of the substance.

There is still further provided, in accordance with a preferred embodiment of the present invention, a device for facilitating passage of a substance through skin on the body of a subject, including:
- an electrode; and
- a control unit, adapted to:
  - drive the electrode to apply to the skin a current capable of ablating stratum corneum epidermidis of the skin, so as to facilitate transdermal passage of the substance,
  - detect generation of at least one spark responsive to application of the current, and
  - modify a parameter of the current responsive to detecting the generation of the at least one spark.

In a preferred embodiment, the control unit is adapted to terminate application of the current responsive to detecting the generation of the at least one spark. Alternatively or additionally, the control unit is adapted to determine whether a number of sparks generated responsive to the applied current exceeds a threshold number. Further alternatively or additionally, the control unit is adapted to determine whether a rate of spark generation responsive to the applied current exceeds a threshold rate.

There is also provided, in accordance with a preferred embodiment of the present invention, a device for facilitating passage of a substance through skin on the body of a subject, including:
- an electrode, a first portion of which having a first cross-section, and a second portion of which having a second cross-section which is different from the first cross-section, the electrode being adapted to be placed such that the first portion is in contact with the skin; and
- a control unit, adapted to drive the electrode to apply an electric current to the skin capable of ablating stratum corneum epidermidis thereof, so as to facilitate passage through the skin of the substance.

Preferably, the control unit is adapted to detect a transition from (a) a first time, in which the second portion is substantially not in contact with the skin, to (b) a second time, in which the second portion is in contact with the skin. Typically, the second portion is electrically conductive. Alternatively, the second portion is substantially electrically non-conductive. Still further alternatively, the second portion includes a partially non-conductive material.

In a preferred embodiment, the second cross-section has a characteristic diameter larger than a characteristic diameter of the first cross-section.

The first portion is typically adapted for insertion into the skin responsive to ablation of the stratum corneum.

In a preferred embodiment, the control unit is adapted to modify a parameter of the current responsive to detecting the transition.

For some applications, the second portion includes the substance.

There is additionally provided, in accordance with a preferred embodiment of the present invention, a device for facilitating passage of a substance through skin on the body of a subject, including:
- a longitudinal electrode, including:
  - a first portion, having a first property at a first longitudinal site of the electrode, and
  - a second portion, having a second property at a second longitudinal site of the electrode, the second property being different from the first property, the electrode being adapted to be placed such that the first portion is in contact with the skin; and
- a control unit, adapted to drive the electrode to apply an electric current to the skin capable of ablating stratum corneum epidermidis thereof.

Preferably, the control unit is adapted to detect a transition from (a) a first time, in which the second portion is substantially not in contact with the skin, to (b) a second time, in which the second portion is in contact with the skin.

In a preferred embodiment, the second portion includes a measured quantity of the substance.

The first portion typically has an electrical property, and the second portion has an electrical property different from the electrical property of the first portion. Alternatively or additionally, the first portion has a material property, and wherein the second portion has a material property different from the material property of the first portion.

Preferably, the control unit is adapted to modify a parameter of the current responsive to detecting the transition.

There is yet additionally provided, in accordance with a preferred embodiment of the present invention, a device for facilitating delivery of a substance through skin on the body of a subject, including:

an electrode, including the substance; and a control unit, adapted to drive the electrode to apply to the skin a current capable of ablating stratum corneum epidermidis of the skin, so as to facilitate delivery of the substance from the electrode through the skin.

There is still additionally provided, in accordance with a preferred embodiment of the present invention, a device for facilitating passage of a substance through skin on the body of a subject, including:

a housing;

an ablating electrode, fixed to the housing and adapted to apply a current to the skin capable of ablating stratum corneum epidermidis in a vicinity of the ablating electrode, so as to facilitate transdermal passage of the substance; and a non-ablating electrode, fixed to the housing and adapted to provide a return path for the current, substantially without ablating stratum corneum in a vicinity of the non-ablating electrode.

Preferably, the ablating electrode includes at least 100 ablating electrodes. And the non-ablating electrode includes at least 3 non-ablating electrodes. Alternatively, the non-ablating electrode includes two non-ablating electrodes, and the device includes a control unit, adapted to measure electrical impedance between the two non-ablating electrodes.

There is also provided, in accordance with a preferred embodiment of the present invention, a device for facilitating passage of a substance through skin on the body of a subject, including:

an electrode, adapted to be applied to the skin;

a mechanical sensor, adapted to detect an indication of a contact force between the electrode and the skin and to generate a sensor signal responsive thereto; and a control unit, adapted to receive the sensor signal and, responsive thereto, to drive the electrode to apply a current to the skin capable of ablating stratum corneum epidermidis thereof, so as to facilitate transdermal passage of the substance.

There is further provided, in accordance with a preferred embodiment of the present invention, a device for facilitating passage of a substance through skin on the body of a subject, including:

an electrode; and a control unit, adapted to drive the electrode to apply current to the skin in a series of bursts, so as to ablate stratum corneum epidermidis of the skin and facilitate transdermal passage of the substance.

Preferably, the control unit is adapted to provide a time period between successive bursts sufficient to allow recovery, at least in part, of a skin property changed by the application of the current.

Preferably, the control unit is adapted to provide a time period between successive bursts sufficient to allow recovery, at least in part, of a level of electrical impedance of the skin that is changed by the application of the current.

In a preferred embodiment, the control unit is adapted to measure an electrical property of the skin during one or more of the bursts, and to modify a parameter of the current responsive to measuring the property. For example, the control unit may be adapted to compare a value of the property measured during one of the bursts with a value of the property measured during another one of the bursts, and to modify a parameter of the current responsive to comparing the values. Alternatively or additionally, the control unit may be adapted to detect, during a single burst, a change in a value of the property, and to modify the parameter of the current responsive to detecting the change.

Typically, the control unit is adapted to provide a period between two of the bursts which is greater than about 1 millisecond and less than about 50 milliseconds.

There is still further provided, in accordance with a preferred embodiment of the present invention, a device for facilitating passage of a substance through skin on the body of a subject, including:

a housing;

an electrode coupled to the housing, the electrode including:

a first portion, adapted for insertion into the skin, and a second portion, adapted to remain outside the skin, and to convey a compressive force from the housing to the skin; and a control unit, adapted to drive the electrode to apply a current to the skin capable of ablating stratum corneum epidermidis of the skin, so as to facilitate passage of the substance through the skin.

Preferably, a characteristic diameter of the second portion of the electrode is such as to inhibit insertion of the second portion into the skin.

For some applications, the second portion is substantially non-conductive.

Preferably, the control unit is adapted to detect contact of the second portion and the skin, and to terminate the current responsive thereto, so as to inhibit insertion of the second portion into the skin.

In a preferred embodiment, the control unit is adapted to detect one or more sparks generated responsive to the current.

The present invention will be more fully understood from the following detailed description of the preferred embodiments thereof, taken together with the drawings in which:

BRIEF DESCRIPTION OF THE DRAWINGS

FIGS. 9A, 9B, 10, and 11 are graphs showing experimental results obtained using apparatus provided in accordance with respective preferred embodiments of the present invention;

DETAILED DESCRIPTION OF PREFERRED EMBODIMENTS

Figure 1:
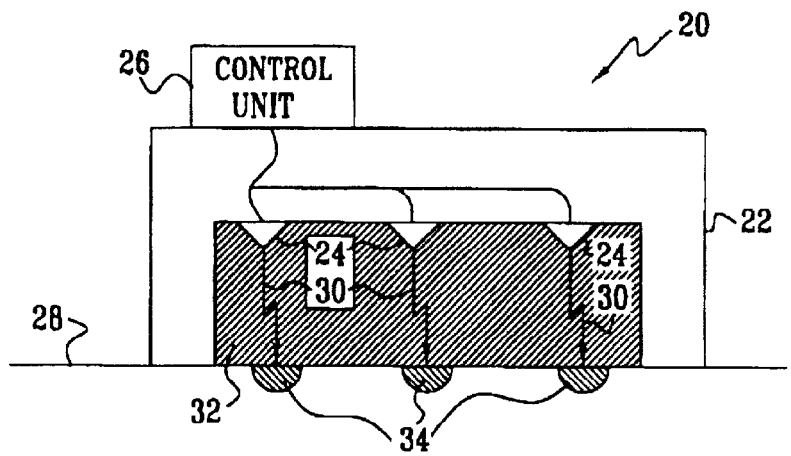
FIG. 1 is a schematic, sectional illustration of a device for transdermal transport of a substance, in accordance with a preferred embodiment of the present invention.

FIG. 1 is a schematic, sectional illustration of a device 20 for facilitating transdermal delivery of an active substance 32 and, optionally, transdermal extraction of an analyte, in accordance with a preferred embodiment of the present invention. Device 20 comprises a housing 22, to which is coupled a control unit 26 and one or more spark-generating electrodes 24. Preferably, during operation of device 20, housing 22 is held in contact with the skin 28 of a subject, such that electrodes 24 are maintained at a generally fixed distance above the skin. In a preferred embodiment, electrodes 24 are between about 5–500 microns above skin 28, although it will be appreciated that the distance may be greater or less than this range, as appropriate, so as to optimize the operation of device 20 for a given application. Typically, each of electrodes 24 comes to a sharp point, so as to facilitate spark generation.

Control unit 26 preferably provides electrical energy to electrodes 24 such that one or more sparks 30 occur between electrodes 24 and skin 28. In a preferred embodiment, regulation of the magnitude and timing of the voltage applied to electrodes 24 controls the strength and number of sparks 30. Preferably, an alternating voltage is applied to electrodes 24, such that a series of sparks 30 occur during a given time interval, with each successive spark ablating more of the stratum corneum. In a preferred embodiment, the alternating voltage has a frequency between about 10 kHz and 4000 kHz, preferably between about 10 kHz and 500 kHz.

For some applications, the voltage is applied for a fixed length of time, determined in advance to be sufficient to achieve the desired degree of ablation. Alternatively or additionally, the number of sparks 30 is counted, and the voltage is turned off after a given number of sparks occur. Typically, when control unit 26 is regulating voltage, a current surge can be detected at the time that a spark is generated. Alternatively, when control unit 26 is regulating current, a detectable voltage drop occurs responsive to spark generation. It is noted that, depending on the properties of the electric field applied to electrodes 24 and the physical construction of device 20, it may be appropriate to detect only a single spark, indicative of ablation of the stratum corneum, or to continue applying the field until, for example, 100 or more sparks are detected.

In a preferred embodiment, a high-magnitude DC voltage is applied to electrodes 24. Preferably, the degree of ablation is controlled by the strength of the applied voltage and/or the number of sparks 30 generated. As described hereinabove, the occurrence of sparks may be determined by current spikes through electrodes 24. Alternatively or additionally, a voltage drop at one of electrodes 24 may be used to determine the occurrence of a spark.

Preferably, housing 22 is adapted to hold a prescribed quantity of a pharmaceutical substance such as an active substance 32, and to passively or actively deliver active substance 32 to a vicinity of one or more spark-induced ablation sites 34 in skin 28. Active substance 32 typically comprises an inactive gel or paste which supports an active pharmaceutical agent, and is applied to housing 22 in a region thereof near electrodes 24. In this manner, as device 20 is held against skin 28, the active substance is also brought into contact with skin 28, so as to be able to pass into the skin upon the ablation thereof. If appropriate, techniques such as iontophoresis, electroporation, sonophoresis, or other methods known in the art may be adapted to further facilitate transdermal transport of substance 32 into the skin, or transport of an analyte out of the skin.

Alternatively, active substance 32 is stored in a porous material, such as a standard medical patch, which is adapted to fit around or in a vicinity of electrodes 24. Further alternatively, no pharmaceutical agent is stored in device 20, but is instead applied, if appropriate, following the ablation of the skin by the device. Still further alternatively, device 20 is used exclusively for ablation of stratum corneum of skin 28 to facilitate analyte extraction, and substantially no active substance is applied to the skin.

Figure 2:
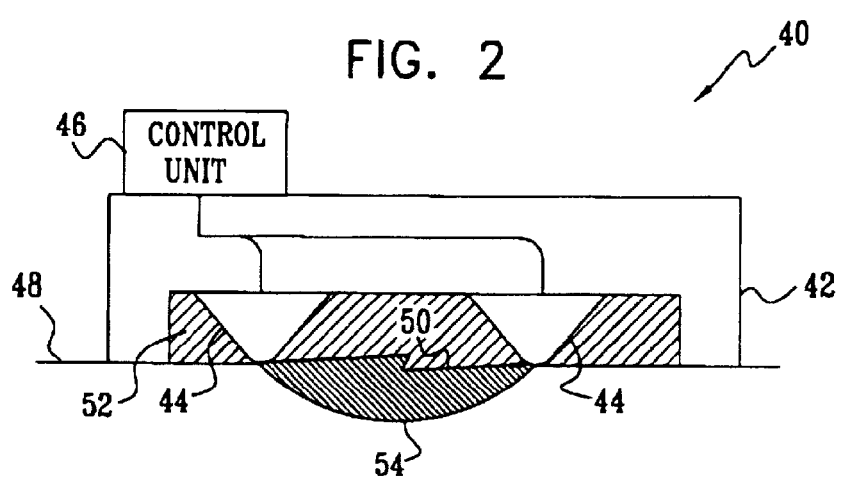
FIG. 2 is a schematic, sectional illustration of another device for transdermal transport of a substance, in accordance with a preferred embodiment of the present invention.

FIG. 2 is a schematic, sectional illustration of another device 40 for facilitating transdermal delivery of a pharmaceutical substance such as an active substance 52 and, optionally, transdermal extraction of an analyte, in accordance with a preferred embodiment of the present invention. Device 40 comprises a housing 42, to which is coupled a control unit 46 and one or more electrodes 44. Preferably, the placement of housing 42 on skin 48 of the subject automatically places electrodes 44 in contact with skin 48, as shown in FIG. 2. Preferably, each one of electrodes 44 has a characteristic diameter of approximately 10–100 microns where it contacts the skin. It is noted that this contact area is significantly smaller than that used for electroporation applications.

For some applications, electrodes 44 function as monopolar electrodes, whereby electrical energy is discharged from electrodes 44 into skin 48, while the return path of the electrical current passes through a much larger surface area (e.g., a metal base of housing 42 surrounding or adjacent to electrodes 44), resulting in substantially no damage to tissue other than in regions near electrodes 44. Alternatively or additionally, when a larger number of electrodes 44 are included in device 40 (e.g., three or more), it may be desirable for one of electrodes 44 to act as an ablating electrode, and for two or more of the other electrodes to act, in combination, as non-ablating "return" electrodes, each conveying a fraction of the ablating current back to control unit 46. Further alternatively or additionally, two relatively large return electrodes are provided, to obtain the safety and other benefits known in the art to be associated with "split grounds." Still further alternatively or additionally, one or more pairs of electrodes 44 are driven in a bipolar mode (as shown in FIG. 2), in which a spark 50 occurs between electrodes 44 in the pair, resulting in ablation of skin 48 in a region 54 thereof.

Control unit 46 preferably functions in generally the same manner as control unit 26 described hereinabove with reference to FIG. 1. Additionally, delivery of active substance 52 to skin 48 is preferably performed in substantially the same manner as the delivery of active substance 32.

Figure 3:
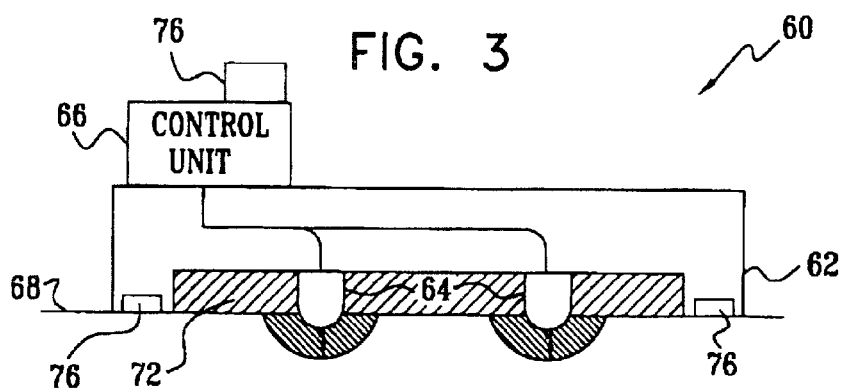
FIG. 3 is a schematic, sectional illustration of yet another device for transdermal transport of a substance, in accordance with a preferred embodiment of the present invention.

FIG. 3 is a schematic, sectional illustration of yet another device 60 for facilitating transdermal delivery of a pharmaceutical substance such as an active substance 72 and, optionally, transdermal extraction of an analyte, in accordance with a preferred embodiment of the present invention. Device 60 comprises a housing 62, to which is coupled a control unit 66 and one or more electrodes 64. Preferably, the placement of housing 62 on skin 68 of the subject causes electrodes 64 to be pressed against skin 68, resulting in dimpling of the skin caused by pressure of the electrodes on the skin. The electrodes preferably extend to a depth of approximately 10–500 microns in the skin, and, as a result, typically maintain contact with the skin during the ablation thereof for a greater time period than do the electrodes shown in FIGS. 1 and 2, for applications in which this is desirable.

Device 60 preferably comprises at least one force/pressure-sensitive switch 76 coupled to control unit 66. The subject is instructed that sufficient pressure must be applied to housing 62 in order for the control unit to activate electrodes 64. Switch 76 thus typically ensures that sufficient pressure is applied to electrodes 64, such that the electrodes depress skin 68 the desired amount and electrical contact or small electrode-skin gap distances are maintained.

For some applications, device 60 is operative to generate sparks in order to ablate skin 68. Alternatively, device 60 drives current into skin 68 in order to ablate the stratum corneum. In a preferred driving mode, sparks are substantially not generated during the ablation, or are only generated after a significant portion of the stratum corneum has been ablated, and therefore serve as a form of electrical feedback to indicate the ablation of the stratum corneum.

Figure 4:
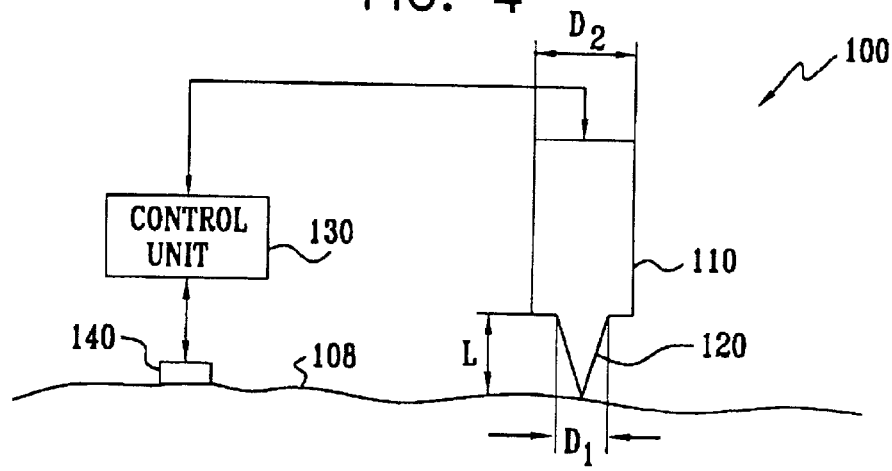
FIGS. 4–7, 8A, 8B, and 8C are schematic, sectional illustrations of electrodes and associated apparatus for ablating stratum corneum, in accordance with respective preferred embodiments of the present invention.

FIG. 4 (not to scale) is a sectional, schematic illustration of an electrode 100 which may be incorporated into any of the devices described hereinabove, in accordance with a preferred embodiment of the present invention. Preferably, a generally conical tip 120 of the electrode is intended for insertion in the skin 108 of the subject up to the tip's entire length L of approximately 10–150 microns (typically about 10–20 microns). A conductive or non-conductive base 110 of electrode 100 preferably has a diameter D2 between about 100 and 500 microns, and meets tip 120 where the tip has a diameter D1 of approximately 20–200 microns. Typically, but not necessarily, D2 is greater than D1 by about 10–500 microns. Although conical tip 120 of electrode 100 is shown as coming to a sharp point, other shapes are suitable for some applications. For example, the tip may be rounded at the point of contact with the skin, such that an equivalent radius of the rounded portion is between about 10 and 100 microns. Alternatively, the tip may be hemispherical, e.g., with a radius of 50 microns. Preferably, a characteristic diameter of the tip is between about 20 and 200 microns. Ablation of the stratum corneum by such a tip advantageously yields channels which are sufficiently large to allow the delivery or extraction therethrough of substantially all pharmaceutical substances and analytes of interest. It is noted that many prior art mechanical devices for puncturing the stratum corneum (particularly those involving needles) have characteristic diameters of approximately 1 micron, and typically: (a) do not provide sufficient depth control, (b) are difficult to manufacture, (c) are slender and can easily break, and/or (d) can cause pain, because of the high probability of significant penetration beyond the stratum corneum and/or because of the high pressure applied by the sharp tips of the needles.

A control unit 130 coupled to electrode 100 preferably comprises one of the control units described hereinabove with reference to FIGS. 1–3. In a preferred application, while tip 120 is being inserted into the skin (facilitated by the ablation thereof), control unit 130 is operative to continuously or intermittently measure the electrical impedance between electrode 100 and a second electrode 140, which is typically significantly larger than electrode 100, and which is placed in electrical contact with skin 108. (Electrode 100 is shown in FIG. 4 just prior to its initial insertion into the skin.)

Experiments performed by the inventors have shown relatively sharp changes in impedance when electrode 100 is inserted the distance L into skin 108, i.e., when the larger face of base 110 of electrode 100 is pressed against the skin. In a preferred embodiment, control unit 130 is adapted to track changes in the impedance of the skin or in another electrical property, in order to receive feedback indicating the depth of insertion of tip 120. For example, control unit 130 may apply current in high-frequency AC bursts, and measure skin impedance during the bursts and/or between bursts, in order to determine the insertion depth of tip 120 or the extent to which the skin has been ablated. For some applications, the control unit modifies a parameter (e.g., amplitude, duration, frequency) of the current applied through electrode 100 responsive to the detected insertion depth of tip 120. Alternatively, the current is turned on or off at the time that base 110 reaches the skin, or shortly thereafter.

Figure 5:
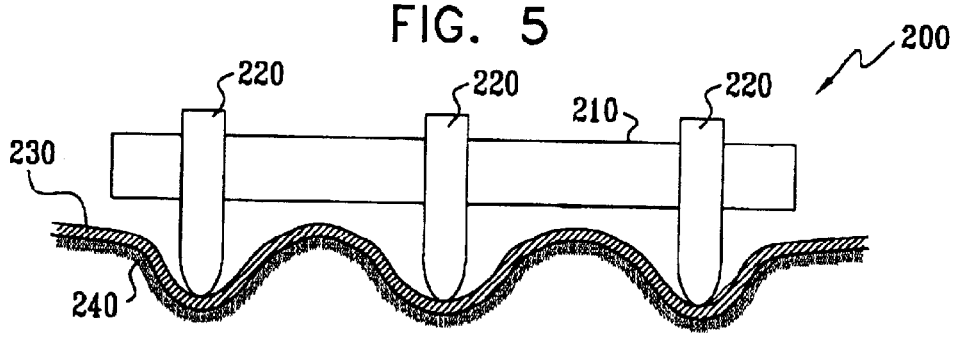

FIG. 5 is a schematic, sectional illustration of a portion of a device 200 for facilitating transdermal delivery of a pharmaceutical substance and/or transdermal extraction of an analyte, in accordance with a preferred embodiment of the present invention. Device 200 preferably comprises a housing 210, which provides support to one or more electrodes 220 to allow the electrodes to apply pressure to the stratum corneum 230 of the subject's skin.

For some applications, electrodes 220 pass through all or a substantial portion of stratum corneum 230 during the ablation thereof, preferably without being subsequently inserted beyond a predetermined distance into underlying epidermal tissue 240. In order to achieve this goal, electrodes 220 typically extend from the base of housing 210 approximately 40–500 microns, which is substantially greater than the 10–50 micron thickness of stratum corneum 230. The added length of the electrodes, while not itself being used for insertion into the skin, has been found by the inventors to be useful because it applies a mechanical force on the skin sufficient to facilitate the entry of the electrodes during ablation. Without the added length, by contrast, the skin would typically be pressed by (and would therefore recede from) an electrode that extends no further from its housing than approximately 50 microns. Such a short electrode would not be subject to the level of reaction force from the skin that is experienced by longer electrodes (e.g., electrodes 220), which are provided by these embodiments of the present invention. The greater reaction force applied to electrodes 220, in turn, facilitates the entry of the electrodes into the stratum corneum.

Alternatively or additionally, the inventors have found that the spacing between each of electrodes 220 contributes in a significant fashion to the level of reaction force of the skin on each of the electrodes. In order to maximize this force, it is generally preferable to maintain a minimum inter-electrode spacing of about 0.3 mm–2mm, and/or about 100%–500% of the total distance from the bottom surface of housing 210 to the tips of electrodes 220. It is to be understood, however, that maximizing the force is not necessarily the only consideration in the design of device 200, and that, for some applications, it is desirable to place the electrodes at a spacing less than that which would maximize the force.

Figure 6:
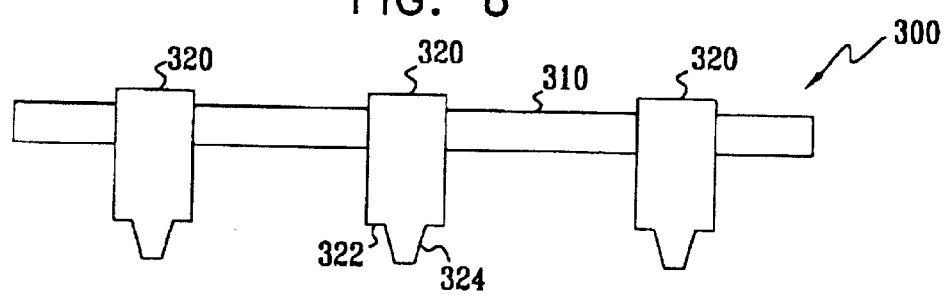

FIG. 6 is a schematic, sectional illustration of a portion of a device 300 for facilitating transdermal delivery of a pharmaceutical substance and/or transdermal extraction of an analyte, in accordance with a preferred embodiment of the present invention. Device 300 preferably comprises a non-conductive housing 310 coupled to one or more stepped electrodes 320. Typically, electrodes 320 each comprise a tip 324, intended for ablation-facilitated insertion into the skin of the subject, and a conductive face 322, at the end of tip 324.

It is noted that although many electrodes are described herein as being "stepped," either by themselves or in combination with the housing or other portions of a device including the electrodes, other shapes not necessarily defining a sharp step are also useful for applying the principles of the present invention. These other shapes could also be configured, for example, to have cross-sections which also provide feedback to a control unit regarding depth of insertion of an electrode. Alternatively or additionally, other changes besides cross-sectional changes may be integrated into the electrodes, such as gradual or sharp changes in an electrical or chemical property. In a preferred embodiment, a pharmaceutical substance for delivery into the skin is placed on a portion of the electrode, such that a control unit can determine when that portion comes in contact with the skin, or reaches a certain depth in the skin. For example, the substance may be configured to be highly conductive or highly resistive to current flow.

A control unit (not shown) coupled to the electrodes is preferably enabled to detect a rapid change in the electrical properties of the electrode/skin interface at the time when conductive face 322 comes in contact with the skin. For example, the control unit may measure the electrical impedance between two of the electrodes, or between one of electrodes 320 and a non-ablating electrode that is in contact with the skin. Experiments conducted by the inventors have shown that these and/or other properties can change within less than about one millisecond following the successful complete insertion of the tip of the electrode into the skin. Advantageously, detecting changes in these properties can be used as feedback to the control unit, e.g., to allow the control unit to terminate current application following such a complete insertion.

It is noted that other forms of electrical feedback may also be utilized, in combination with or separately from directly detecting the contact of face 322 with the skin. For example, spark generation may be detected, which has been found by the inventors to typically be initiated or accelerated following generally complete insertion of tip 324. It is hypothesized that increased spark generation is observed following contact of face 322 with the skin, because further current application ablates and thereby removes tissue below the electrode, whereupon the continued presence at tip 324 of a high voltage, in the absence of a suitable resistive path for current flow, results in the generation of sparks between the tip and the skin. Thus, increased spark generation is an indicator of the contact of face 322 with the skin.

Figure 7:
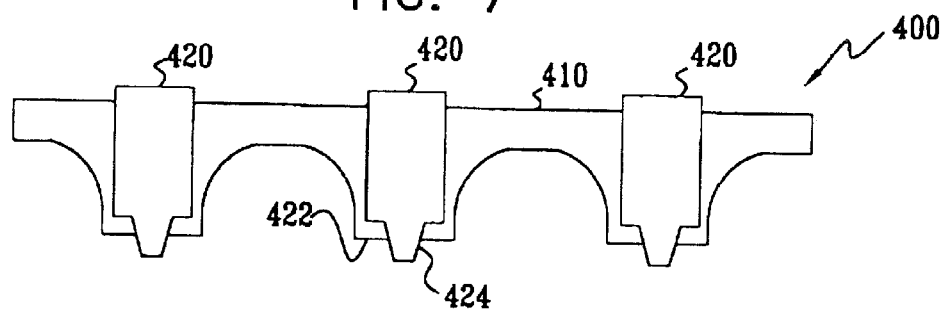

FIG. 7 is a schematic, sectional illustration of a portion of a device 400 for facilitating transdermal delivery of a pharmaceutical substance and/or transdermal extraction of an analyte, in accordance with a preferred embodiment of the present invention. Device 400 preferably comprises a non-conductive housing 410, through which protrude the tips 424 of one or more electrodes 420, in order to make contact with the skin of the subject. Typically, the length of the portion of tip 424 which protrudes through housing 410 is between approximately 10 and 200 microns, and is preferably about 50–60 microns. Following insertion of at least a portion of tip 424 into the skin (facilitated by ablation of the stratum corneum), a non-conductive face 422 of housing 410 comes into contact with the skin, typically inhibiting by virtue of its size any further insertion of the electrode. For some applications, the properties of face 422 are obtained, alternatively, by applying a non-conductive coating to electrode 420. In a preferred embodiment, the diameter of non-conductive face 422 is at least about 40 microns greater than the diameter of tip 424 where it meets face 422. Typically, the diameter of face 422 is about 40–200 microns greater than the diameter of tip 424 where it meets face 422.

Advantageously, even without the impedance changes described with reference to FIG. 6, spark generation may in any case typically be detected, and may further provide a feedback to the control unit (not shown) indicating complete insertion. It is noted that considerable benefit is derived from the use of a "step" from tip 424 to non-conductive face 422, which would not be obtained were housing 410 to simply have a series of 50–60 micron electrodes protruding from its lower surface. In particular, the distance of face 422 from the lower surface of electrode housing 410 is typically at least about 100 microns, and the total distance from the lower surface of housing 410 to the end of tip 424 is typically between about 40 and 500 microns. Thus, as described hereinabove with reference to FIG. 5, this total distance allows device 400 to apply a sufficient amount of force to the skin in order to facilitate the entry of the electrode during ablation of the stratum corneum.

Figure 8A:
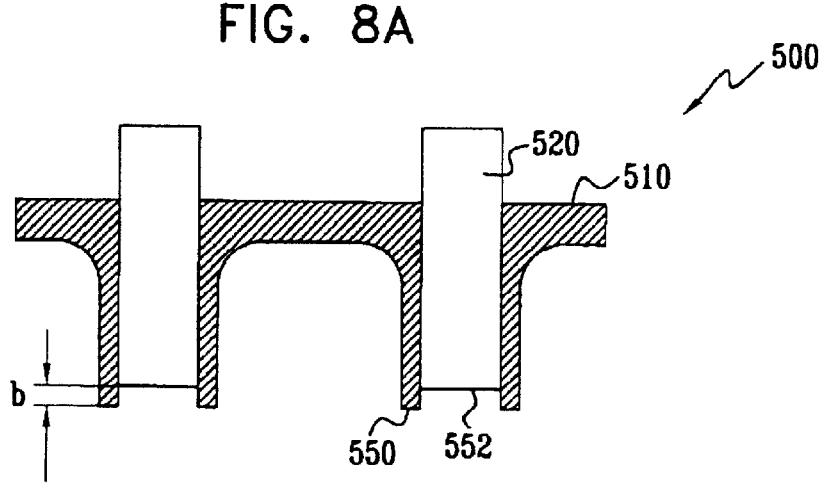

FIG. 8A is a schematic illustration of a portion of a device 500 for facilitating transdermal delivery of a pharmaceutical substance and/or transdermal extraction of an analyte, in accordance with a preferred embodiment of the present invention. Preferably, device 500 comprises a non-conductive frame 510, a surface 550 of which is placed against the skin of the subject. An electrode 520, recessed a distance b within the frame (typically about 5–500 microns), is driven by a control unit to apply current to the skin. Because the tip 552 of electrode 520 is recessed within the frame, the current is typically delivered to the skin in the form of a series of one or more sparks, whose number and/or rate are preferably regulated by the control unit so as to obtain ablation of the stratum corneum within a suitable time period.

Figure 8B:
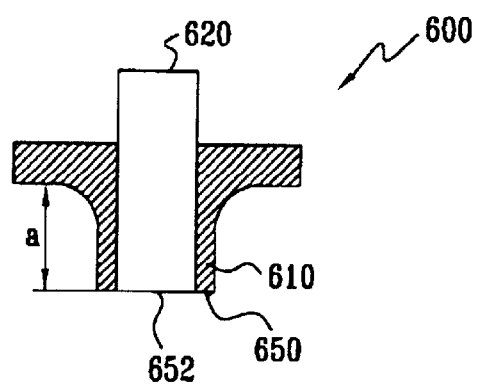

FIG. 8B is a schematic illustration of a portion of a device 600 for facilitating transdermal delivery of a pharmaceutical substance and/or transdermal extraction of an analyte, in accordance with a preferred embodiment of the present invention. Preferably, device 600 comprises a non-conductive frame 610, a skin-contact surface 650 of which is placed against the skin of the subject. A distance"a" of about 40 to 500 microns preferably separates the underside of frame 610 from the skin-contact surface. An electrode 620, a surface 652 of which is generally flush with surface 650, is driven by a control unit to apply current to the skin. This current is preferably initially delivered directly to the skin, and, after the ablation of some or all of the stratum corneum, terminated following the generation of one or more sparks.

Figure 8C:
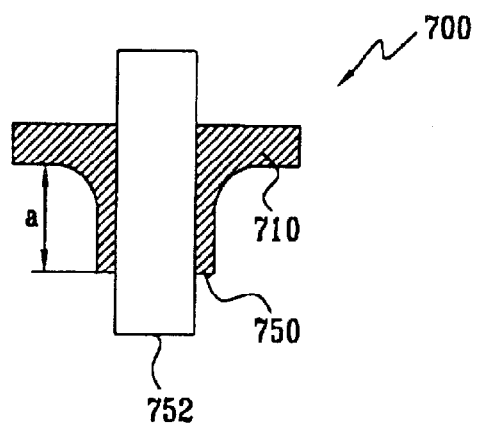

FIG. 8C is a schematic illustration of a portion of a device 700 for facilitating transdermal delivery of a pharmaceutical substance and/or transdermal extraction of an analyte, in accordance with a preferred embodiment of the present invention. Preferably, device 700 comprises a non-conductive frame 710, a surface 750 of which is placed against the skin of the subject. An electrode fixed to frame 710 preferably comprises a surface 752 which protrudes beyond surface 750 by a distance sufficient to obtain the advantages of direct current application followed by sparks (described hereinabove with reference to FIGS. 4–7).

Reference is now made to FIGS. 9A and 9B. FIG. 9A is a graph showing experimental data measured during a period in which an electrode was in generally continuous contact with in vitro skin taken from behind the ear of a pig, in accordance with a preferred embodiment of the present invention. A 100 kHz sinusoidal voltage was applied by the electrode to the skin, and it is seen that during the first millisecond, the current delivered to the skin increased, peaked, and began to decrease until a generally steady-state current injection period began at approximately 2.5 milliseconds. FIG. 9B shows some of the same data as in FIG. 9A, on an expanded time scale.

It is hypothesized that changes in electrical properties of the skin may be responsible, at least in part, for the observed changes in the waveform of FIG. 9A. For example, it may be that the relatively high impedance seen at the beginning of the application of current is reduced during the first millisecond because of ablation of the stratum corneum, and, perhaps, because of a generally simultaneous release of water from intracellular and/or interstitial sources. correspondingly, it may be that the decrease in current and the final steady-state waveform result from essentially complete local ablation and desiccation in an area adjacent to the tip of the electrode, whereby further current flow is significantly impeded. (FIG. 10, described hereinbelow, shows that if during this period the applied voltage is sufficiently high, then spark generation occurs, because spark discharge does not require a path of conductive material.) It will be appreciated, however, that other mechanical, electrical, or physiological explanations of the observed data may also be correct.

Further experimental data (not shown) have shown that providing a short period without energy application is typically sufficient in order to reduce the impedance and facilitate further unimpeded ablation, when the same driving voltage is reapplied. Each such "burst" of energy application typically yields generally the same characteristic rise, fall, and steady-state behavior of the measured current, although the later bursts generally reach successively higher peak currents. Preferably, each burst includes an AC component having a characteristic frequency between about 10 kHz and 500 kHz. Burst durations from about 10 microseconds to 100 milliseconds (typically ranging from 100 microseconds to 10 milliseconds) are preferred, with particular values typically being selected in combination with the selection of other driving parameters, such as frequency and signal amplitude and electrode shape. Inter-burst periods preferably range from about 100 microseconds to 100 milliseconds.

Figure 10:
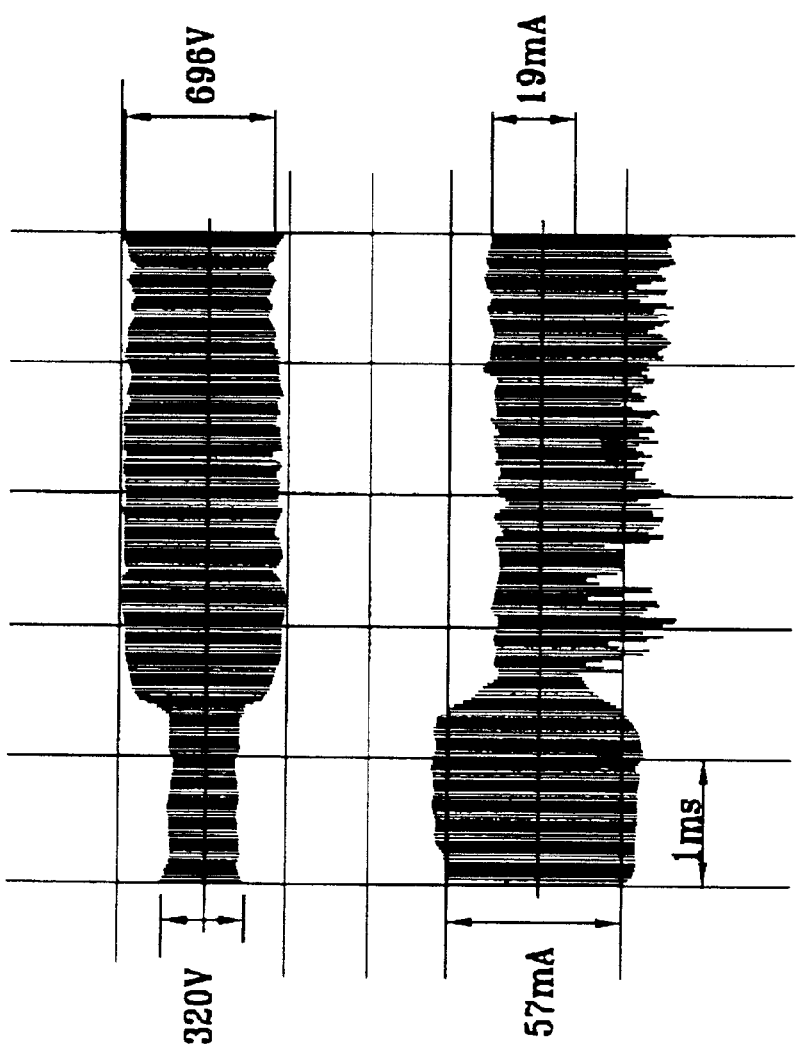

FIG. 10 is a graph showing experimental data measured during the insertion into skin of an experimental electrode similar to electrode 100 (FIG. 4), in accordance with a preferred embodiment of the present invention. In particular, the experimental electrode was constructed to have a 30 micron diameter stainless steel tip. A second electrode was placed on the skin at a distance of 15 mm from the experimental electrode. A non-ideal voltage source drove the electrode to apply to the skin a 100 kHz biphasic signal, which was designated to be 700 V, but, because of the high 57 mA peak-to-peak current drain, was measured to be 320 V peak-to-peak.

Following contact of the base of the experimental electrode with the skin, the measured peak-to-peak current dropped to 19 mA, allowing the applied voltage to recover to a measured peak-to-peak voltage of 696 V. In addition, a large number of sparks were observed, which correspond to the downward moving current spikes seen in FIG. 10. It is hypothesized that the sparks were generated as a result of a self-nurturing cycle, in which ablation causes gaps to form between the electrode and the skin, which induce more sparks, additional ablation, and yet further gaps.

Figure 11:
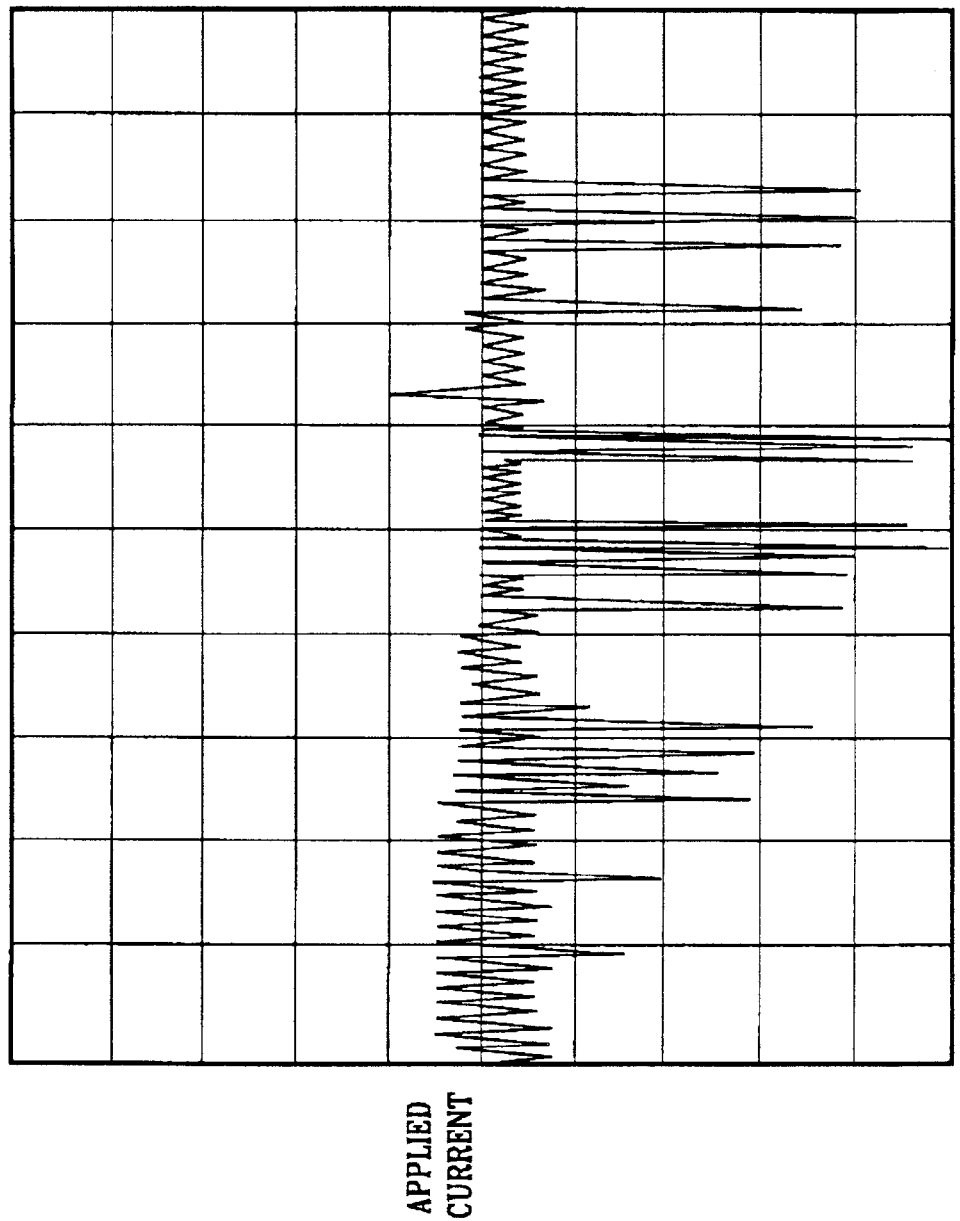
Figure 12:
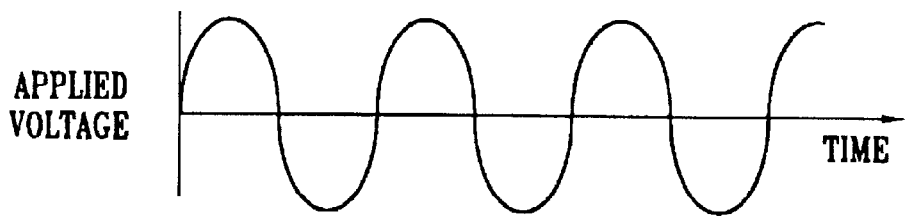
FIGS. 12–15 are graphs schematically illustrating waveforms for application to tissue, in accordance with respective preferred embodiments of the present invention.
Figure 13:
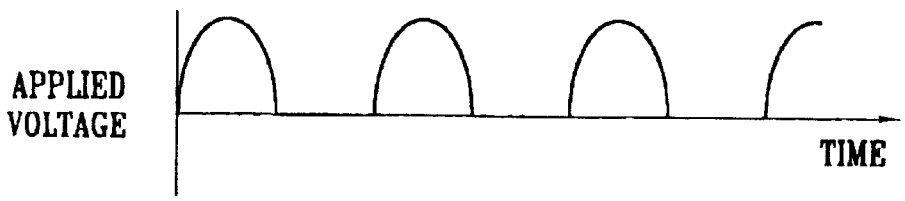
Figure 14:
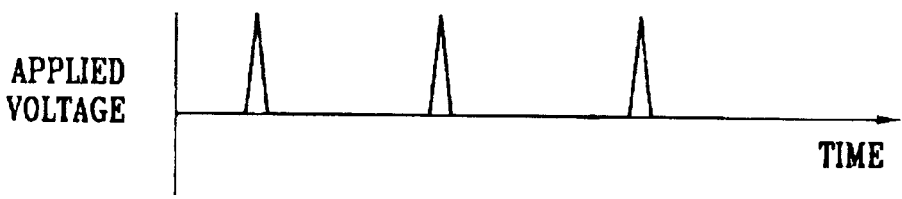
Figure 15:
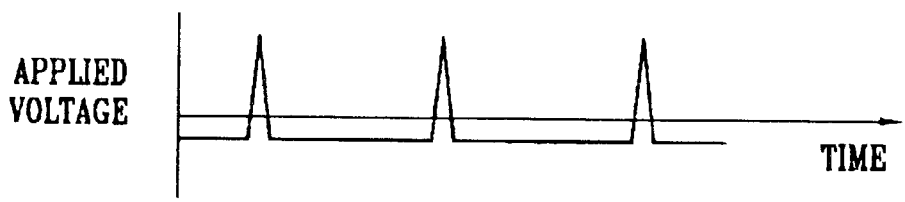

FIG. 11 is a graph showing experimental data obtained during ablation of in vitro stratum corneum from a pig, in accordance with a preferred embodiment of the present invention. A large number of spark discharges can be seen in the figure, and, in a preferred embodiment, a control unit such as one of those described hereinabove is operative to detect these spikes using signal processing techniques known in the art, and to regulate the application of energy to the skin responsive thereto.

Reference is now made to FIGS. 12, 13, 14, and 15, which are schematic illustrations of different waveforms for application to the skin of a subject, in accordance with respective preferred embodiments of the present invention. For some applications, it is generally preferable to apply a symmetric sinusoid (FIG. 12) having no DC component, as this minimizes pain. For other applications, however, it is preferred to apply a half sine wave (FIG. 13) or a series of pulses (FIG. 14), as these typically allow the generation of higher voltages by some power sources that are well-suited for use with these applications. Alternatively, a series of pulses having the net DC component removed (FIG. 15) may be applied. Still further alternatively, other waveforms are selected for application to the skin, responsive to the type of material which is to be conveyed through the skin, energy considerations, and/or the area of the skin to which a device is applied.

Figure 16:
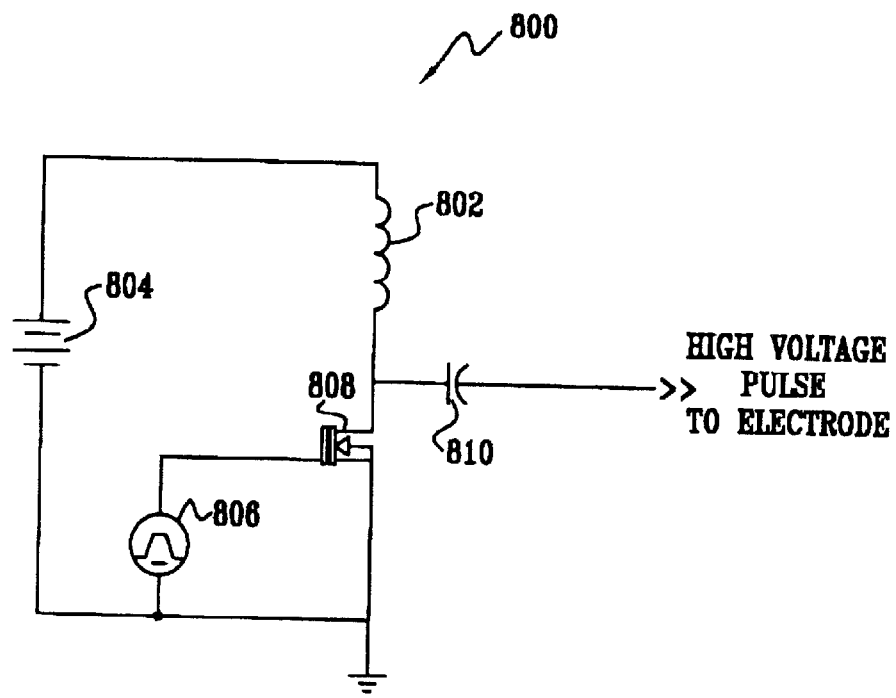
FIGS. 16 and 17 are schematic illustrations of circuitry for use in accordance with respective preferred embodiments of the present invention.

FIG. 16 is a schematic illustration of circuitry 800 for generating high voltages for application to the skin, in accordance with a preferred embodiment of the present invention. Circuitry 800 preferably comprises a DC voltage source 804 coupled to supply power to a low-voltage pulse generator 806, whose pulses are amplified and conveyed to an ablating electrode via the coupling of generator 806 to an inductor 802, a MOSFET 808, and a capacitor 810.

Figure 17:
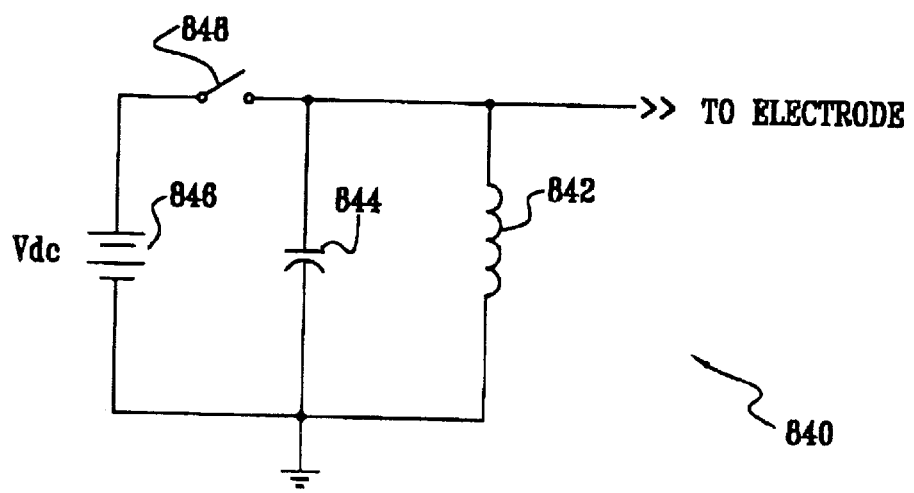

FIG. 17 is a schematic illustration of resonant circuitry 840 for generating high voltages for application to the skin, in accordance with another preferred embodiment of the present invention. Circuitry 840 preferably comprises a DC voltage source 846 coupled through a controlled switch 848 to generate an AC signal, whose frequency is determined by the values of a capacitor 844 and an inductor 842 in the circuit. Resonant circuits are particularly well-suited for some applications of the present invention, because they have inherent self-limiting behaviors, such as changes in resonant gain as electrode insertion and ablation causes impedance changes.

It will be appreciated that the circuitry shown in FIGS. 16 and 17 may be supplemented or replaced, as appropriate, with other circuitry known in the art for generating high voltages, such as transformers or voltage multipliers.

Figure 18:
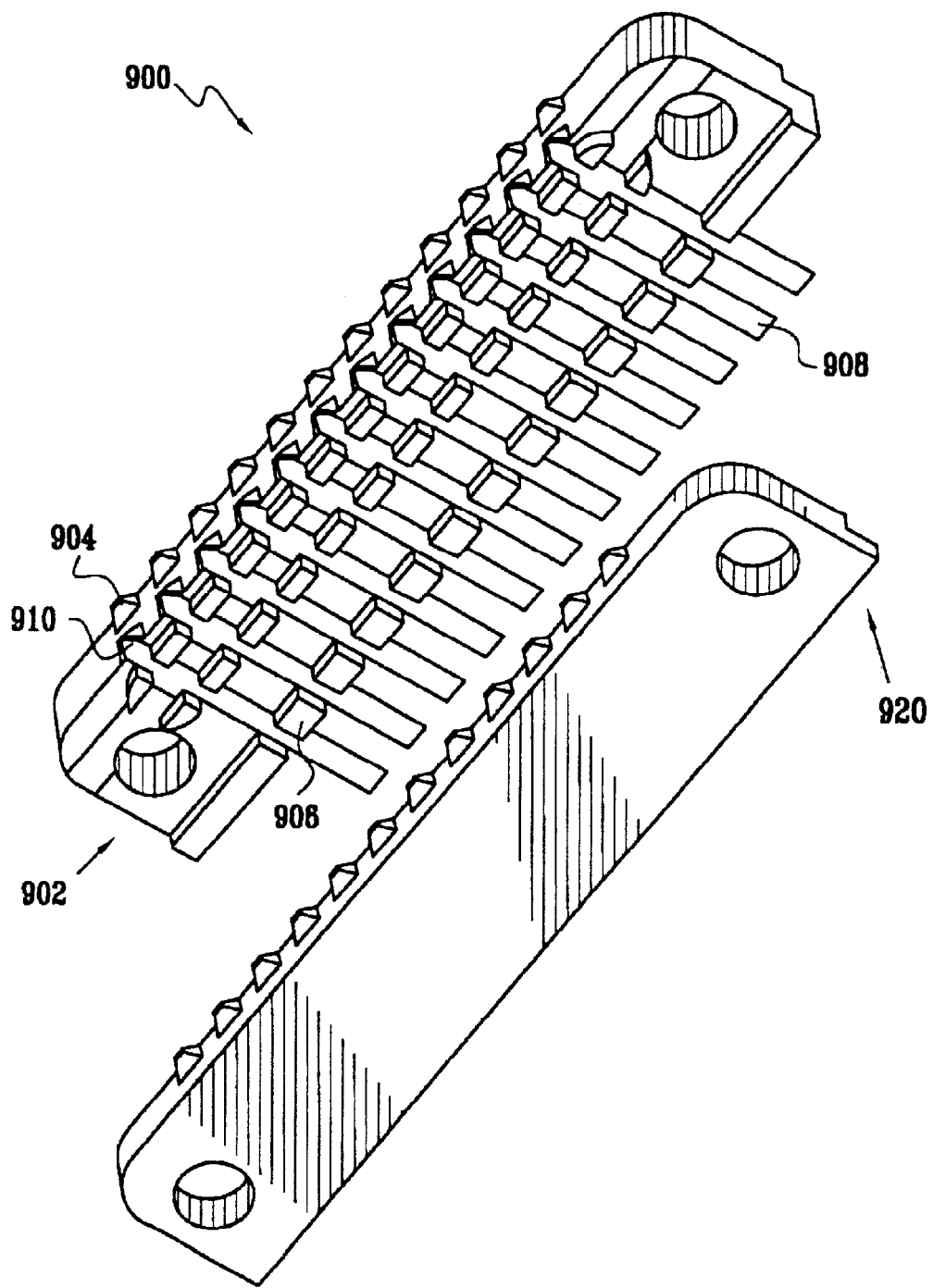
FIG. 18 is a schematic illustration of an assembly for ablating stratum corneum, in accordance with a preferred embodiment of the present invention.

FIG. 18 is a schematic illustration of a device 900 for facilitating transdermal delivery of a pharmaceutical substance and/or transdermal extraction of an analyte, in accordance with a preferred embodiment of the present invention. Device 900 preferably comprises an endplate 920, a series of one or more electrode mounting elements 902, and a second endplate 920 (not shown). In use, elements 902 are preferably securely sandwiched between the two endplates.

Element 902 preferably comprises a series of electrodes 908. Twelve such electrodes are shown in the figure. In a preferred embodiment, the length of each electrode 908 (extending from a first end which is square to a skin-contact end 910 which is typically generally pointed) is approximately 4–5 mm, and the width at the first end is about 0.4 mm. The first end of each electrode is typically electrically coupled to a control unit. Preferably, mechanical supporting members 906 surround and maintain the position of each electrode 908. Pyramid-style pieces 904 on element 902 (or pieces having other shapes) preferably engage corresponding pieces 904 on endplate 920 or on an adjacent element 902, in order to surround part or all of skin-contact end 910 of each electrode and provide the "step" feature described hereinabove.

For some applications, electrodes 908 and/or other electrodes described herein may comprise stainless steel or titanium, and may be formed from sheets having a thickness ranging from about 10 to 200 microns. Techniques known in the art may be used for forming the electrodes from these sheets, such as through the use of laser cutting.

Figure 19:
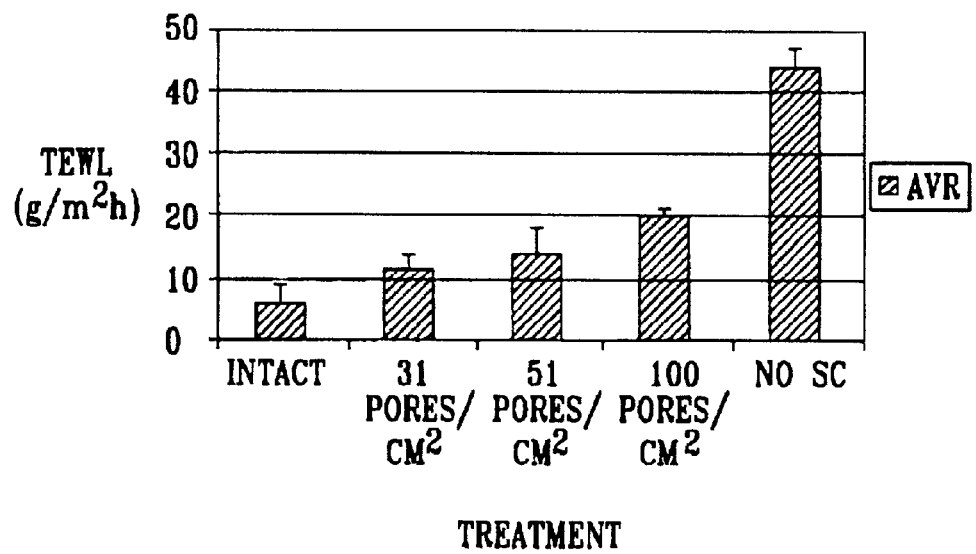
FIGS. 19–23 are graphs showing experimental data obtained during using techniques provided in accordance with respective preferred embodiments of the present invention.
Figure 20:
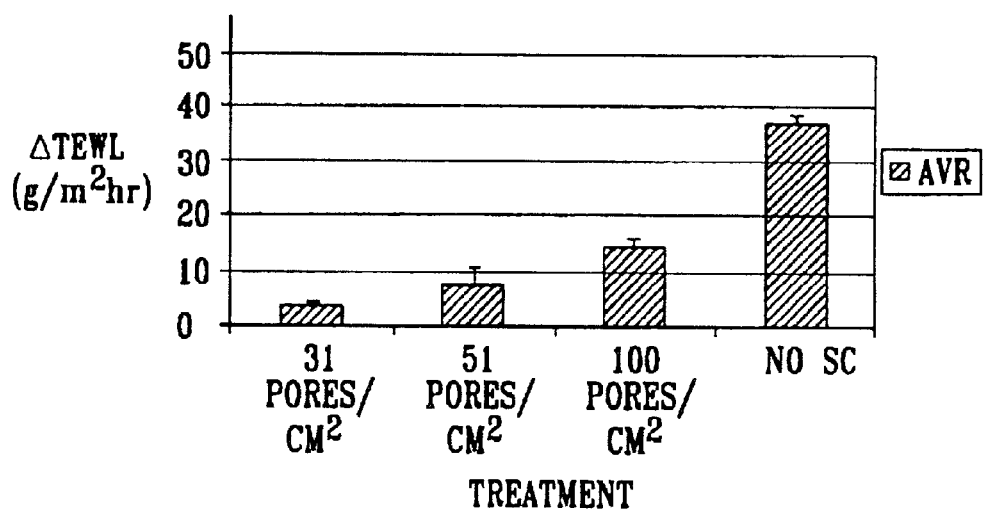

Reference is now made to FIGS. 19 and 20, which are graphs showing experimental results obtained using techniques provided in accordance with respective preferred embodiments of the present invention. The parameter Transepidermal Water Loss (TEWL) was evaluated in order to assess the extent of the creation of micropores in the outer layers of the skin. For these experiments, frozen pig ear skin was placed overnight in refrigeration, and than transferred to room temperature for at least 1 hour. Values of TEWL presented in FIG. 19 represent:

(a) intact skin (n=8), (b) skin after poration (31, 51 or 100 pores/cm2) induced by ablation of the stratum corneum, as provided by embodiments of the present invention (n=5), and (c) stratum corneum (SC) elimination (by forcibly stripping off the stratum corneum using 25 applications and removal of sticky tape) (n=9).

Another measure of the effect of these embodiments of the present invention is seen by evaluating the change in TEWL caused by the different treatments (FIG. 20). Both figures show a strong correlation between pore density (as determined by electrode density) and elevation in TEWL.

Figure 21:
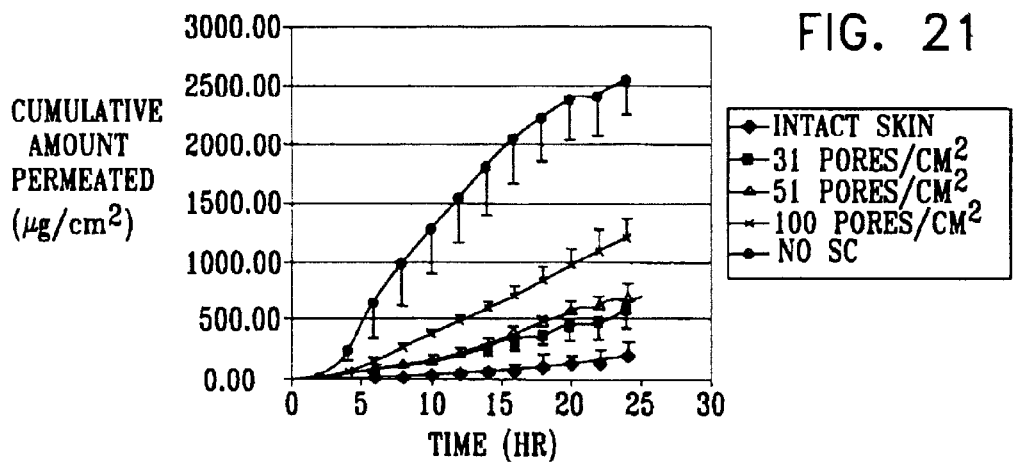
Figure 22:
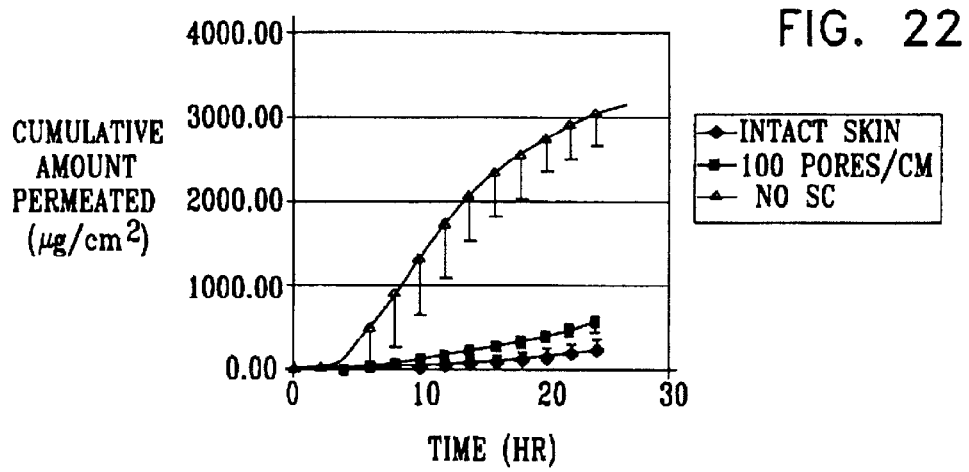
Figure 23:
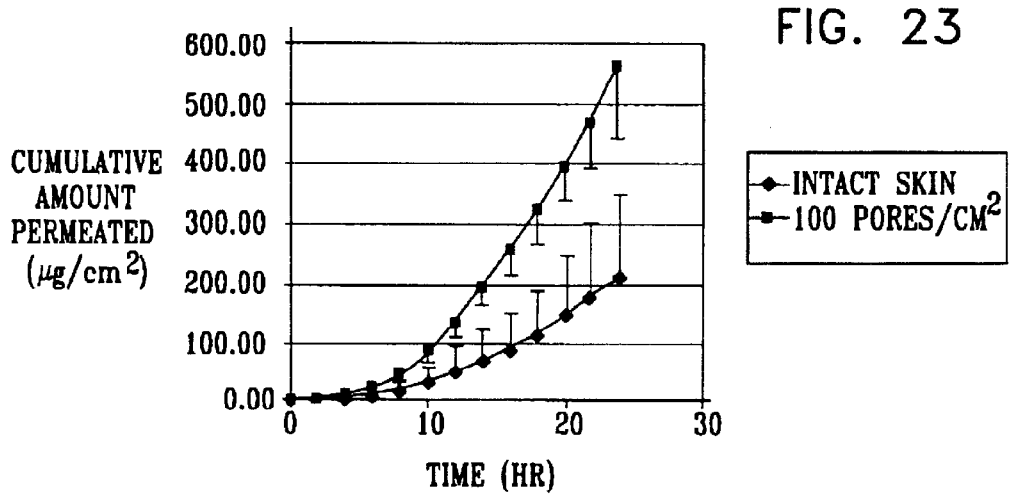

Reference is now made to FIGS. 21, 22, and 23, which are graphs showing experimental results obtained using techniques provided in accordance with respective preferred embodiments of the present invention. The permeation of drugs through pig ear skin was studied using flow-through diffusion cells (LGA Inc., Berkeley, Calif.). Each cell had a diffusional surface area of 3.1 cm2 and a receptor volume of 5 ml. The temperature of the receptor compartment was maintained at 33° C. A donor solution placed in a cell on one side of the skin sample comprised 1% acetaminophen in 10% ethyl alcohol. The receptor solution, in the cell on the other side of the skin sample, comprised 10% ethyl alcohol in PBS (pH 7.2). A flow rate of 2 ml/hr was maintained. Permeation results for acetaminophen are shown in FIG. 21 for intact skin (n=5 diffusion cells), 31 and 51 pores/cm2 (n=5), 100 pores/cm2 (n=4), and no stratum corneum (i.e., tape-stripped skin) (n=7).

Pore creation, in accordance with the ablation technique of a preferred embodiment of the present invention, is seen to have enhanced the permeation of acetaminophen through the skin compared to untreated skin. Moreover, the density of 100 pores/cm2 resulted in a 10-fold elevation in drug permeation compared to untreated skin. It is also noted that FIG. 21 shows a direct correlation between pore density and permeation enhancement.

In similar tests with diclofenac (FIGS. 22 and 23), the donor solution had 1% diclofenac in 10% ethyl alcohol, and the receptor solution was PBS (pH 7.2). The flow rate was maintained at 2ml/hr. The results of the diclofenac study are shown in FIGS. 22 and 23 for intact skin (n=4), 100 pores/cm2 (n=4), and tape-stripped skin (n=4). Skin treated using the ablation techniques provided by embodiments of the present invention so as to have a density of 100 pores/cm2 displayed a 2.5 elevation in drug permeation compared to the untreated group. In tape-stripped skin, the permeation was much higher than both the intact and the pored skin, indicating that for diclofenac, it may be appropriate to induce an even higher pore density in order to attain significantly higher permeation values.

It is to be understood that the techniques described herein for transdermal delivery of a substance are generally appropriate for many types of substances, including drugs, and broadly including any active agents that include chemical or biological compounds produced either by chemical synthesis or biotechnology routes, including fermentation and/or recombinant technologies.

These drugs may be used or administered to humans or animals or to laboratory animals as an aid in the diagnosis, treatment or prevention of disease or other abnormal conditions, or for the relief of pain or suffering or to control or improve any physiologic or pathologic condition, or for lifestyle improvement, e.g., via cosmetic substances. Drug delivery devices provided by these embodiments of the present invention can be used for administering drugs that are physiologically or pharmacologically active at a point in near relation to the drug delivery device, or for administering a systemically active substance which will produce a physiological or pharmacological response at a site remote from the point of application of the drug delivery device.

The active agents that can be administered by these devices include, therefore, by way of illustration and not limitation:

drugs acting on the immune system, e.g., immunosupressants including Cyclosporine, Sirolimus, Tacrolimus, Mycophenolate Mofetil, central nervous system and anti-dementia drugs including Venlafaxine, Risperidone, Ziprasidone and Flumazenil, L-DOPA; hypnotics, sedatives, and Dopamine agonists, including Bromocriptine, Cabergoline, Pergolide, Pramipexole; Anti-Alzheimer products, including Donepezil, Rivastigmine and Tacrine, Non-Steroidal Anti-Inflammatory and other non-opioid analgesics including Diclofenac (also for topical uses), Acelofenac, Bromfenac, Darbufelone, Dexketoprofen, Diflunisal, Fentoprofen, Floctafenine, Flubiprofen, Ibuprofen, Indomethacin, Ketoprofen, Etodolac, Meclofenamate, Mefenamic acid, Meloxicam, Naproxen, Nabumetone, Phenylbutazone, Piroxicam, Oxprazosin, Sulindac, Tenoxicam, Tiaprofenic acid, Tolmetin, Ketorolac, Narcotic analgesics, including Fentanyl, Anileridine, Buprenophine, Apomorphine, Butarophol, Codeine, Hydrocodone, Hydromorphone, Levorphanol, Meperidime, Methadone, Morphine, Nalbuphine, Opium, Oxycodone, OxyMorphone, Pentazocine, Propoxyphene, Parenteral anesthetics including Atricaine, Lidocaine, Bupivacaine, Chloroprocaine, Etidocaine, Levobupivacaine, Mepivacaine, Prilocaine, Procaine, Tetracaine, Rpivacaine, Cox-2 inhibitors, including Rofecoxib, Celecoxib, and Tramadol, Antimigraine drugs including Sumatriptan, Naratriptan, Zolmitriptan, Rizatriptan, Eletriptan, Almotriptan and Frovatriptan, products designated for neuropathic pain management, including Gabapentin, Pergabalin, drugs useful for alcoholism addiction treatment, including Disulfiram, Naltrexone, LevoMethadyl, post-operative nausea and vomiting products, including Ondansetron, Granisetron, Dolasetron, Nasasetron, Lerisetron, Palonosetron, Tropisetron, Dorabinol, anticoagulants designed for injection, including Heparin, Enoxaparin, Tinzaparin, Antagonists platelet aggregation inhibitors, Eptifibatide, Tirofiban, Dipyridamole, Peripherally-acting compounds, including Prazosin, Terazosin, Tamsulosin, Doxazosin, BHP treatment drugs, including Finasteride, Bone calcium regulators, e.g., those designated to treat osteoporosis, including Etidronate, Alendronate, Pamidronate, Tiludronate, Clodronate, Ibadronate, Drugs for the treatment of type II diabetes including Rosiglitazoen, Gemcitabine, Glimpride, Miglitol, Acarbose, Rosiglitazone, Products designated to treat attention deficit disorder—MethylPhenydate, Cardiovascular products, including ACE inhibitors and Beta blockers and additional drugs including Tobramycin, Defferoxamine, Argatroban, Mitoxantrone, Anagrelide, Caspofungin, Trisenox, Therapeutic proteins and peptides, including Calcitonin, Desmopressin, Gonadorelin, LHRH, Goserelin, Histerelin, Leuprolide, Lypressin, Nafarelin, Octreotide, Oxytocin, Pentagastrin, Secretin, Vassopressin, Insulin, Sex hormones, e.g., to treat aging symptoms or for use as contraceptives, including Testosterone, Estrogen, Progesterone, Dehydroepiandrosterone, recombinant biopharmaceuticals, including Erythropoietin, Filgrastim, Insulin, Interferon-A, Interferon-B, Energix-B, Interferon Beta, Growth Hormone, Abciximab, Etanercept, Enbrel, vaccines, nucleotide drugs, including oligonucleotide drugs, polynucleotide drugs hydrophilic compounds, e.g., those which are typically impeded from passing through the stratum corneum, and gene therapy agents, based on DNA, RNA and antisense RNA.

These drugs as well as other substances can be prepared using known techniques, and then used with devices provided by embodiments of the present invention.

It is to be appreciated that whereas, by way of illustration and not limitation, some preferred embodiments of the present invention are described with respect to providing the housing as a return path for current flow, other parts of the devices, such as specially-designated electrodes, may also provide the return path.

It is to be understood that—except where it is explicitly noted otherwise or where it is implicit from context—the methods and apparatus described herein with respect to facilitating substance delivery into the skin may typically be adapted for analyte extraction applications, *mutatis mutandis*, and, similarly, methods and apparatus described herein with respect to facilitating analyte extraction may be adapted for substance delivery applications, *mutatis mutandis*. In addition, some devices incorporating embodiments of the present invention may include means for both drug delivery and analyte extraction, and, if appropriate, apparatus within the device for analyzing the analyte and controlling aspects of the drug delivery responsive to the analysis.

It is further to be understood that elements of the various aforementioned devices that are described as being non-conductive may, for some applications, be partly conductive or even highly conductive, and that electrical properties of the devices may be expected to be modified responsive thereto.

It is noted that the figures depicting preferred embodiments of the present invention are not necessarily drawn to scale, and, instead, change certain dimensions in order to more clearly demonstrate some aspects of the invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A device for facilitating passage of a substance through skin on the body of a subject, comprising:
   an electrode, a first portion of which having a first cross-section, and a second portion of which having a second cross-section which is different from the first cross-section, the electrode being adapted to be placed such that the first portion is in contact with the skin; and
   a control unit, adapted to drive the electrode to apply an electric current to the skin capable of ablating stratum corneum epidermidis thereof, so as to facilitate passage through the skin of the substance.

2. A device according to claim 1, wherein the control unit is adapted to detect a transition from (a) a first time, in which the second portion is substantially not in contact with the skin, to (b) a second time, in which the second portion is in contact with the skin.

3. A device according to claim 2, wherein the second portion is electrically conductive.

4. A device according to claim 1, wherein the second portion is substantially electrically non-conductive.

5. A device according to claim 1, wherein the second portion comprises a partially non-conductive material.

6. A device according to claim 1, wherein the second cross-section has a characteristic diameter larger than a characteristic diameter of the first cross-section.

7. A device according to claim 1, wherein the first portion is adapted for insertion into the skin responsive to ablation of the stratum corneum.

8. A device according to claim 2, wherein the control unit is adapted to modify a parameter of the current responsive to detecting the transition.

9. A device according to claim 1, wherein the second portion comprises the substance.

10. A device for facilitating passage of a substance through skin on the body of a subject, comprising:
    a longitudinal electrode, comprising:
    a first portion, having a first property at a first longitudinal site of the electrode, and
    a second portion, having a second property at a second longitudinal site of the electrode, the second property being different from the first property, the electrode being adapted to be placed such that the first portion is in contact with the skin; and a control unit, adapted to drive the electrode to apply an electric current to the skin capable of ablating stratum corneum epidermidis thereof.

11. A device according to claim 10, wherein the control unit is adapted to detect a transition from (a) a first time, in which the second portion is substantially not in contact with the skin, to (b) a second time, in which the second portion is in contact with the skin.

12. A device according to claim 10, wherein the second portion comprises a measured quantity of the substance.

13. A device according to claim 11, wherein the first portion has an electrical property, and wherein the second portion has an electrical property different from the electrical property of the first portion.

14. A device according to claim 11, wherein the first portion has a material property, and wherein the second portion has a material property different from the material property of the first portion.

15. A device according to claim 11, wherein the control unit is adapted to modify a parameter of the current responsive to detecting the transition.

* * * * *